US012383497B2

(12) United States Patent
Dusci

(10) Patent No.: US 12,383,497 B2
(45) Date of Patent: Aug. 12, 2025

(54) READY-TO-USE PHENYLEPHRINE FORMULATIONS AND PRODUCTS

(71) Applicant: INFORLIFE SA, Campascio (CH)

(72) Inventor: Sergio Dusci, Tresivio (IT)

(73) Assignee: INFORLIFE SA, Campascio (CH)

( * ) Notice: Subject to any disclaimer, the term of this patent is extended or adjusted under 35 U.S.C. 154(b) by 0 days.

(21) Appl. No.: 18/775,679

(22) Filed: Jul. 17, 2024

(65) Prior Publication Data
US 2025/0099381 A1 Mar. 27, 2025

Related U.S. Application Data

(60) Provisional application No. 63/515,050, filed on Jul. 21, 2023.

(51) Int. Cl.
| | |
|---|---|
| *A61K 9/08* | (2006.01) |
| *A61J 1/14* | (2023.01) |
| *A61K 31/137* | (2006.01) |
| *A61K 47/02* | (2006.01) |
| *A61K 47/12* | (2006.01) |

(52) U.S. Cl.
CPC ............... *A61K 9/08* (2013.01); *A61J 1/1475* (2013.01); *A61K 31/137* (2013.01); *A61K 47/02* (2013.01); *A61K 47/12* (2013.01)

(58) Field of Classification Search
None
See application file for complete search history.

(56) References Cited

U.S. PATENT DOCUMENTS

| | | |
|---|---|---|
| 11,213,480 B1 | 1/2022 | McAnany et al. |
| 11,471,400 B2 | 10/2022 | McAnany et al. |
| 2021/0228507 A1* | 7/2021 | Puri ............... B65D 75/38 |
| 2022/0023201 A1* | 1/2022 | McAnany ............ A61K 47/12 |

OTHER PUBLICATIONS

Sandoz Canada Inc., Phenylephrine Hydrochloride Injection USP, Jan. 13, 2011 (6 pages).
Excela, Vazculep (phenylephrine hydrochloride) Injection for intravenous use Initial U.S. Approval: 1954, Oct. 2019 (10 pages).
Fresenius Kabi, Phenylephrine Hydrochloride injection, for intravenous use Initial U.S. Approval: 1954, Mar. 2018 (2 pages).
Meitheal, Phenylephrine Hydrochloride injection, for intravenous use Initial U.S. Approval: 2012, Nov. 2019 (2 pages).
Hikma, Immphentiv® (phenylephrine hydrochloride) injection for intravenous bolus use only Phenylephrine Hydrochloride injection, for intravenous use Initial U.S. Approval: 2012, Mar. 2023 (11 pages).
"Parenteral Preparations: Formulation Challenges", Mfg. Chemist (Feb. 6, 2017); 8 pages.
"Do You Know the Difference Between Extractables and Leachables?", Azenta Life Sci. (Jul. 10, 2019); 6 pages.
"Temporary Policies for Compounding Certain Parenteral Drug Products Guidance for Industry", FDA-Compounding, (Oct. 2024) 18 pages.

* cited by examiner

*Primary Examiner* — Alton N Pryor
(74) *Attorney, Agent, or Firm* — Rothwell, Figg, Ernst & Manbeck, P.C.

(57) ABSTRACT

The invention includes a phenylephrine product including an aqueous phenylephrine solution, a tonicity adjusting agent, at least one pH adjusting agent, at least one buffering agent and water for injection, wherein the phenylephrine solution is does not comprise sodium metabisulfite, wherein the phenylephrine product is sterile and ready-to-use and contain an oxygen absorber to keep the oxygen dissolved below 1 ppm. The invention includes methods of making and using the phenylephrine product.

27 Claims, 6 Drawing Sheets

READY-TO-USE PHENYLEPHRINE FORMULATIONS AND PRODUCTS

CROSS-REFERENCE TO RELATED APPLICATIONS

This application claims priority benefit of U.S. provisional application No. 63/515,050, filed Jul. 21, 2023 the disclosure of which is incorporated herein by reference in its entirety.

TECHNICAL FIELD

The present invention relates to ready-to-use, sterile, premixed formulations of phenylephrine, or a pharmaceutically acceptable salt thereof, that are stable for 24 months or longer at room temperature and can be used, for example, to increase blood pressure in adults with clinically important hypotension resulting primarily from vasodilation, in such settings as septic shock or anesthesia.

BACKGROUND

Phenylephrine hydrochloride is an alpha-1 adrenergic receptor agonist chemically designated benzene methanol, 3-hydroxy-α [(methyl amino) methyl]-hydrochloride (R). Phenylephrine hydrochloride is a sympathomimetic amine that predominantly acts by a direct effect on α-adrenergic receptors. Phenylephrine hydrochloride is indicated for increasing blood pressure in adults with clinically important hypotension resulting primarily from vasodilation, for example in settings including but not limited to septic shock and anesthesia. Phenylephrine is known to experience physical and chemical degradation.

Most preparations of phenylephrine hydrochloride are available as a concentrate solution in 10 mg/ml vial. Phenylephrine formulations that are commercially available and approved by the FDA in the U.S. currently contain Sodium Metabisulfite added as an antioxidant or edetate disodium (ETDA) as a chelating agent.

Phenylephrine can be administered to a patient, for example, for increasing blood pressure in adults with clinically important hypotension resulting primarily from vasodilation, in such settings as septic shock or anesthesia.

The container of a product intended for parenteral use has to ensure continuous compliance with the storage and handling specifications throughout the product shelf life to maintain functionality and drug delivery accuracy. Several factors have to be considered when choosing the right packaging/container for an injectable product, such as drug product formulation properties, dosage, type of application, stability, storage conditions and duration, and end-user friendliness.

There is a need for a sterile, ready-to-use infusion container comprising a stable, liquid formulation of phenylephrine which can be administered to a patient in need thereof without deviation or manipulations and while preserving the sterility of the product, thereby avoiding a compromise with the sterility, an error in dosing accuracy and/or in medicament preparation etc. There is a need for a ready-to-use phenylephrine solution that has a shelf-life of 24 months or more at room temperature. There is a need for a ready-to-use phenylephrine solution that does not comprise an antioxidant such as sodium metabisulfite or a chelating agent such as EDTA.

SUMMARY OF THE INVENTION

In the present invention, the inventors have overcome multiple problems of prior phenylephrine formulations, such as additional costs and inconvenience, the risk of contamination due to inadvertent medical error, and the risk of overdosing or underdosing patients, by providing a phenylephrine product capable of long-term storage in the form of a ready-to-use product containing a stable, sterile phenylephrine solution suitable for infusion directly into a subject. The inventors have developed a ready-to-use, stable, sterile, formulation of phenylephrine hydrochloride in an infusion container that is not terminally sterilized. The inventors have developed a ready-to-use, stable, sterile, formulation of phenylephrine hydrochloride packaged with an oxygen absorber that does not require sodium metabisulfite or another antioxidant or preservative or added chelating agent. The ready-to-use, stable, sterile, formulation of phenylephrine hydrochloride packaged with an oxygen absorber is stable for up to 24 months without either a chelating agent or an antioxidant.

For materials being considered for use as primary packing materials for the infusion container, the challenge has been to develop packaging that is compatible with the contents, minimizes extractables/leachables, is solvent-resistant, and is durable. The packaging of a pharmaceutical product must be compatible with the specific drug and its specific formulation components, and desirably, the packaging and drug formulation should be stable and mutually compatible under aseptic conditions, as packaging materials can affect the condition of different formulations in unpredictable ways. The inventors have beneficially developed a ready-to-use phenylephrine formulation in an infusion bag that is shelf-stable in an infusion container without the use of Sodium Metabisulfite and is sterile without terminal sterilization.

The present invention relates to a premixed pharmaceutical compositions of phenylephrine, or a pharmaceutically acceptable salt thereof. The premixed pharmaceutical compositions of phenylephrine of the present invention are formulated for administration to a patient, without the need to reconstitute or dilute the composition prior to administration, and without the need for terminal sterilization and without use of use of Sodium Metabisulfite or other sulfite-containing compounds.

In certain aspects, the phenylephrine product of the present disclosure comprises an aqueous phenylephrine hydrochloride solution comprising about 0.01 to about 10 mg/ml, about 0.02 to about 8 mg/ml, about 0.03 to about 6 mg/ml, about 0.04 to about 4 mg/ml, about 0.05 to about 3 mg/ml, about 0.06 to about 2 mg/ml, about 0.07 to about 1 mg/ml, about 0.08 mg/ml, about 0.2 mg/ml, or about 0.4 mg/ml phenylephrine hydrochloride, a tonicity adjusting agent, at least one pH adjusting agent, at least one buffering agent, and water for injection in a 250 mL infusion bag. In certain aspects, the phenylephrine product of the present disclosure comprises an aqueous phenylephrine solution comprising phenylephrine as the free base or a pharmaceutically acceptable salt of phenylephrine other than the hydrochloride salt. In those aspects, the concentration of phenylephrine is equivalent to the concentration of phenylephrine in a solution comprising about 0.01 to about 10 mg/ml, about 0.02 to about 8 mg/ml, about 0.03 to about 6 mg/ml, about 0.04 to about 4 mg/ml, about 0.05 to about 3 mg/ml, about 0.06 to about 2 mg/ml, about 0.07 to about 1 mg/ml, about 0.08 mg/ml, about 0.2 mg/ml, or about 0.4 mg/ml phenylephrine as the hydrochloride salt.

In certain aspects, the pharmaceutically acceptable salt is phenylephrine hydrochloride. In one aspect, the tonicity adjustment agent comprises sodium chloride, dextrose, glycerin, glycerol, mannitol, sorbitol, lactose, trehalose, potassium chloride, or a combination thereof.

In some aspects, the buffering agent is selected from sodium citrate dihydrate, citric acid monohydrate, or a combination thereof. In certain aspects, the buffering agent is sodium citrate dihydrate, citric acid anhydrous or a combination thereof. In some aspects, the sodium citrate dihydrate is at a concentration selected from the group 0.08 mg/ml, 0.2 mg/ml and 0.4 mg/ml. In some aspects, the citric acid monohydrate is at a concentration selected from the group 0.032 mg/ml, 0.25 mg/ml and 0.4 mg/ml. In some aspects, the citric acid anhydrous is at a concentration selected from the group 0.007 mg/ml, 0.18 mg/ml and 0.036 mg/ml.

In some aspects, the pH adjusting agent comprises hydrochloric acid, sodium hydroxide, or a combination thereof. In some aspects, a pH adjusting agent may include acetate, citrate, tartrate, histidine, glutamate, phosphate, Tris, glycine, bicarbonate, succinate, sulfate, nitrate, or a combination thereof. In some aspects, the pH of the liquid pharmaceutical composition is about 3 to about 6.5.

In one aspect, the aqueous phenylephrine solution is free of one or more antioxidants. In some aspects, the aqueous phenylephrine solution is free of a chelating agent, free of an antioxidant, free of a complexing agent, and/or free of a preservative.

In one aspect, the aqueous phenylephrine solution has an osmolality of about 270-320 mOsmol/kg. In some aspects, the amount of bacterial endotoxin in the aqueous phenylephrine solution is 25 EU/mg or less.

In one aspect, the phenylephrine product of the present disclosure comprises at least one port. In some aspects, the phenylephrine product of the present disclosure comprises at least two or more ports.

In one aspect, the phenylephrine product of the present disclosure comprises at least one twist-off closure. In some aspects, the twist-off closure comprises low density polyethylene (LDPE), polypropylene (PP), or a combination thereof. In certain aspects, the twist off closure comprises a membrane that creates a barrier, splitting the twist-off closure in two parts. In certain aspects, the twist off closure comprises an inferior part of the membrane in direct contact with the phenylephrine solution, while the superior part is in contact with a zone that forms an air chamber into the closure. In certain aspects, the closure is a rubber stopper. In certain aspects, the closure is made of a plastic material. In certain aspects, the closure is a rubber or silicon stopper. Other closure systems that are stable with low leachables are also contemplated in this disclosure.

In one aspect, the infusion bag comprises at least one port is a tubing port. In some aspects, the tubing port is used to fill the bag with the aqueous phenylephrine solution. In certain aspects, the tubing port comprises one or more layers of a plastic material. In some aspects, the tubing port comprises a PP/ethylene vinyl acetate (EVA) material. In certain aspects, the tube port comprises a multilayer polyolefin and styrene block copolymer tube material. In some aspects, the tubing port comprises a multi-layer co-extruded connector tubing. In some aspects, the tubing port is polyvinyl chloride (PVC)-free and/or plasticizer-free. In some aspects, the tubing port is sealed closed. In some aspect the tubes ports is a single layer plastic material.

In one aspect, the infusion bag comprises a flexible film. In some aspects, the flexible film may be a multilayer film or a single layer film. In some aspects, the innermost layer of the infusion container is made-up of a material that does not show any adsorption of phenylephrine thereby causing no loss of potency and/or assay percentage during preparation, filling sterilization and during storage. In some aspects, the multilayer film may comprise other layers that may be made up of materials such as polyethylene, polypropylene, modified polyolefin-polyethylene polymers, styrene-polyolefin based polymers and block co-polymers thereof etc. In some aspects, the infusion bag comprises a multilayer polyolefin film. In some aspects the infusion bag comprises 2 to 7 layers of polyolefin film. In some aspects, the infusion bag comprises a 5 layer polyolefin film or more than 7 layers.

In one aspect, the primary packaging for the phenylephrine product of the present disclosure is a flexible intravenous bag. In one aspect, the primary packaging for phenylephrine product of the present disclosure is a pre-filled syringe. In one aspect, the primary packaging for the phenylephrine product of the present disclosure is a plastic bottle or semi-flexible IV container. In one aspect, the primary packaging for the phenylephrine product of the present disclosure is a glass container.

In some aspects, the infusion bag further comprises an overwrap. In some aspects, the overwrap comprises polyester, aluminum, polypropylene, or a combination thereof. In some aspects, the overwrap is a plastic overwrap. In some aspects, the infusion bag further comprises an oxygen absorber and an oxygen indicator. In some aspects, the overwrap comprises a transparent strip over the oxygen indicator to allow for reading the oxygen indicator without removing the overwrap.

In one aspect, the phenylephrine or a pharmaceutically salt thereof is chemically stable for at least at least 6 months, at least 12 months, at least 18 months, or at least 24 months when packaged with oxygen absorber and stored at a controlled room temperature in the infusion bag of the present disclosure. In one aspect, the controlled room temperature is 15-30° C. In one aspect, the controlled room temperature is 15-30° C. with relative humidity (RH) at about 40%±5%.

In one aspect, the average number of particles equal to or greater than 10 µm present in the units tested does not exceed 6000 per 250 mL infusion bag when the phenylephrine product of the present disclosure is at room temperature for at least 24 months. In certain aspects, the average number of particles equal to or greater than 10 µm present in the phenylephrine product of the present disclosure units tested does not exceed 600 per container. In certain, the average number of particles equal to or greater than 10 µm present in the phenylephrine product of the present disclosure units tested does not exceed 60 per container. In one aspect, the average number of particles equal to or greater than 25 µm present in the units tested does not exceed 600 per 250 mL infusion bag when the phenylephrine product of the present disclosure is at room temperature for at least 24 months. In one aspect, the average number of particles equal to or greater than 25 µm present in the units tested does not exceed 60 per 250 mL infusion bag when the phenylephrine product of the present disclosure is at room temperature for at least 24 months.

In one aspect, the oxygen content after accelerated stability at 40° C.±2° C./15% RH±5% for 6 months in the aqueous phenylephrine solution of the present disclosure is <=1 ppm about 0.80 ppm. In one aspect, the pH after accelerated stability at 40° C.±2° C./15% RH±5% for 6 months is about 3 to 6.5. In one aspect, the osmolality after accelerated stability at 40° C.±2° C./15% RH±5% for 6 months in the aqueous phenylephrine solution of the present disclosure is about 270-320 mOsmol/kg. In one aspect, the total unknown impurities after accelerated stability at 40° C.±2° C./15% RH±5% for 6 months in the aqueous phenylephrine solution of the present disclosure is less than 0.5%.

In one aspect, the infusion bag is aseptically filled with the aqueous phenylephrine solution with no degassed WFI and under normal atmospheric pressure.

In one aspect, the disclosure provides a method of preparing a phenylephrine product of the present disclosure by: (i) adding phenylephrine or a pharmaceutically salt thereof and one or more buffering agents to water; (ii) adjusting the pH to about 3 to 6.5 using a pH adjusting agent; (iii) adjusting the tonicity of the solution with a tonicity adjusting agent; (iv) filtering the solution of step (iii) in a first sterilizing filtration; (v) filtering the solution of step (iv) in a second sterilizing filtration; (vi) filling the solution into a sterile infusion bag; (vii) sealing the infusion bag of step (vi); and optionally (viii) overwrapping the sealed infusion bag of step (vii) wherein said overwrap comprises an overwrap, an oxygen absorber and oxygen indicator.

In one aspect, the disclosure provides a method of increasing blood pressure in a patient in need thereof, comprising administering an aqueous phenylephrine solution from the phenylephrine product of the present disclosure to the subject. In some aspects, the phenylephrine is administered as a continuous infusion. In one aspect, the phenylephrine solution is administered by an intravenous infusion. In one aspect, the phenylephrine or a pharmaceutically salt thereof is administered at 0.5 mcg/kg/min to 1.4 mcg/kg/min, titrated to effect. In one aspect, the phenylephrine or a pharmaceutically salt thereof is administered at 0.5 mcg/kg/minute to 6 mcg/kg/min, titrated to effect.

In one aspect, the disclosure provides a method of increasing blood pressure in a patient in need thereof, comprising administering an aqueous phenylephrine solution using the phenylephrine product of the present disclosure to the subject. In some aspects, the aqueous phenylephrine solution is administered as an intravenous bolus infusion. In one aspect, 50 mcg (micrograms) to 250 mcg of phenylephrine hydrochloride is administered as an intravenous bolus. In some aspects, an infusion bag contains 20 mg/250 mL (0.08 mg/ml), 50 mg/250 mL (0.2 mg/ml), or 100 mg/250 mL (0.4 mg/ml) phenylephrine hydrochloride, or an equivalent amount of phenylephrine as the free base or another pharmaceutically acceptable salt thereof.

DETAILED DESCRIPTION

Figure 1:
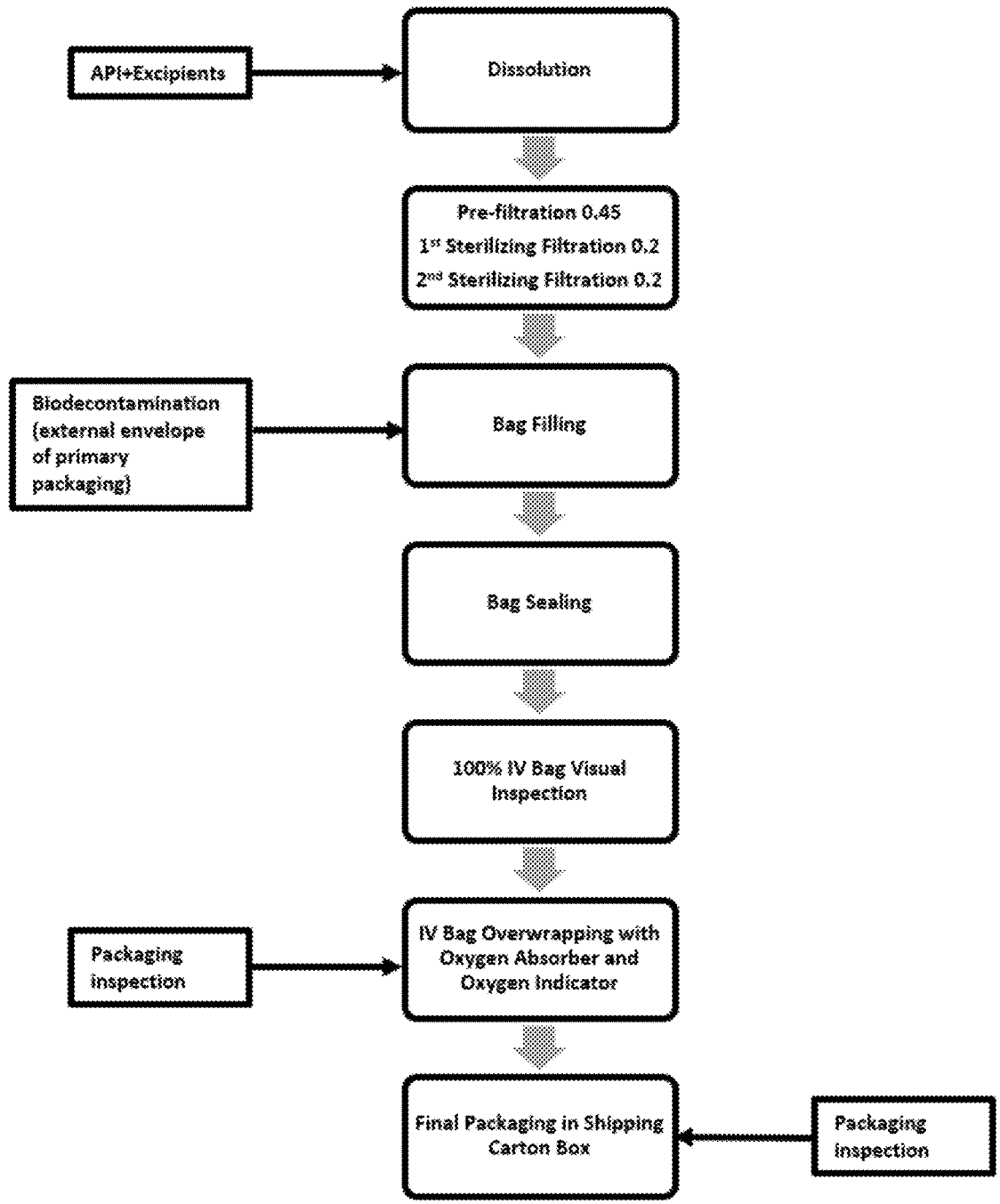
FIG. 1 shows the manufacturing process of the phenylephrine product of the present disclosure.

The present invention involves phenylephrine prepared in a premixed, ready-to-use, formulation that does not require reconstitution or dilution prior to administration to a patient and remains stable and active after prolonged storage. In some aspects, the phenylephrine formulation is contained in an aseptically filled infusion bag. Such premixed formulations avoid the cost, inconvenience, risk of contamination, and inaccurate dosage amounts that can be associated with reconstituting or diluting a concentrated phenylephrine formulation prior to administration to a patient. In some aspects, the present invention includes ready-to-use phenylephrine formulations that do not comprise a sulfite-containing antioxidant but remain sterile and stable when stored at room temperature for a prolonged period (e.g., 24 months or longer periods) after being aseptically filled in an infusion container.

The premixed ready-to-use products and compositions of phenylephrine of the present invention are formulated for administration to a patient without the need to reconstitute or dilute the composition prior to administration.

In certain aspects, the present invention of the disclosure is a phenylephrine product comprising an aqueous phenylephrine solution comprising about 0.08 mg/ml, 0.2 mg/ml or 0.4 mg/ml phenylephrine hydrochloride, a tonicity adjusting agent, at least one pH adjusting agent, at least one buffering agent and water for injection.

In one aspect, the phenylephrine is in the form of the free base or a pharmaceutically acceptable salt. In certain aspects, the pharmaceutically acceptable salt is phenylephrine hydrochloride. In one aspect, the tonicity adjustment agent comprises sodium chloride, dextrose, glycerin, glycerol, mannitol, sorbitol, lactose, trehalose, potassium chloride, or a combination thereof.

In some aspects, the buffering agent is selected from sodium citrate dihydrate, citric acid monohydrate, or a combination thereof. In certain aspects, the buffering agent is sodium citrate dihydrate, citric acid anhydrous or a combination thereof. In some aspects, the sodium citrate dihydrate is at a concentration selected from the group 0.08 mg/ml, 0.2 mg/ml and 0.4 mg/ml. In some aspects, the citric acid monohydrate is at a concentration selected from the group 0.032 mg/ml, 0.25 mg/ml and 0.4 mg/ml. In some aspects, the citric acid anhydrous is at a concentration selected from the group 0.007 mg/ml, 0.18 mg/ml and 0.036 mg/ml.

In some aspects, the pH adjusting agent comprises hydrochloric acid, sodium hydroxide, or a combination thereof. In some aspects, the pH of the liquid pharmaceutical composition is about 3 to 6.5.

In one aspect, the aqueous phenylephrine solution is free of an antioxidant. In some aspects, the aqueous phenylephrine solution is free of a chelating agent, an antioxidant, a stabilizer, and a complexing agent. In certain aspects, the aqueous solution is antioxidant-free (e.g., free of sodium metabisulfite or other antioxidants), but may contain one or more chelating agents, complexing agents, and/or non-antioxidant stabilizers.

In some aspects, the aqueous phenylephrine solution has an osmolality of about 270-320 mOsmol/kg. In some aspects, the amount of bacterial endotoxin in the aqueous phenylephrine solution is 25 EU/mg or less.

In one aspect, the primary packaging for the phenylephrine product of the present disclosure is an intravenous bag. In one aspect, the primary packaging for the phenylephrine product is a pre-filled syringe. In one aspect, the primary packaging for the phenylephrine product is a plastic bottle or semi-flexible IV container. In one aspect, the primary packaging for the phenylephrine product of the present disclosure is a glass container.

In one aspect, the intravenous bag is made up of multi-layer polyolefin film. Such containers are available as Nexcel brand M312 and M312A® films by SealedAir Corporation. In another aspect, the intravenous bag is made up of multilayer polypropylene styrene-block copolymer. Such containers are available commercially under the APP-series film IV bag products manufactured by Polycine, such as APP-114S. In one aspect, the intravenous bag comprises an inner layer made up of a cycloolefin polymer, a middle layer made up of linear low density polyethylene polymer and an outer layer made up of low density polyethylene polymer. Such containers are available commercially available as Polyelite EHC® film bags manufactured by Hosokawa. In another aspect, intravenous bag is made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially under the brand name Inerta 103 and are manufactured by Technoflex. Other commercially-available intravenous bags that are stable, with low leachables.

In some aspects, the infusion bag of the phenylephrine product of the present disclosure comprises at least one port. In some aspects, the infusion bag of the phenylephrine product of the present disclosure comprises at least two ports.

In some aspects, the infusion bag of the phenylephrine product of the present disclosure comprises at least one closure. In certain aspects the closure is a twist-off closure. In certain aspects, the closure comprises a membrane that creates a barrier, splitting the closure in two parts. In certain aspects, the closure comprises an inferior part of the membrane in direct contact with the phenylephrine solution, while the superior part is in contact with a zone that forms an air chamber into the closure. In some aspects, the twist-off closure comprises polyethylene LDPE, polypropylene PP or a combination thereof. In certain aspects, other polymers that are stable, with low leachables, and without physical deformation during exposure to thermal sealing may also be used for the closure. In some aspects, the closure is a rubber plug. In some aspects, the rubber plug provides a fluid tight closure of the passage and a lid member that clamps the periphery of the rubber plug. In one aspect, the rubber plug is a resalable plug which provides fluid tight closure of the passage and a plastic cap that clamps the periphery of the resealable plug. In certain aspects, the closure comprise a plastic material. In certain aspects, the closure is a cap. Other closure systems that are stable with low leachables are also contemplated in this disclosure.

In some aspects, the infusion bag of the phenylephrine product of the present disclosure comprises at least one port that is a tubing port. In some aspects, the tubing port is used to fill the bag with the antioxidant-free aqueous phenylephrine solution. In certain aspects, the tubing port comprises one or more layers of a plastic material. In some aspects, the tubing port comprises a PP/EVA material. In some aspects, the tubing port comprises a multi-layer co-extruded connector tubing. In some aspects, the tubing port is PVC and/or plasticizer free. In some aspects, the tubing port is sealed closed.

In one aspect, the infusion bag comprises a flexible film. In some aspects, the flexible film may be a multilayer film or a single layer film. In some aspects, the infusion bag of the phenylephrine product of the present disclosure comprises a flexible multilayer polyolefin film. In some aspects the infusion bag comprises 2 to 7 layers of polyolefin film. In some aspects, the infusion bag comprises a 5 layer polyolefin film or more than 7 layers. In some aspects, the innermost layer of the infusion container is made-up of a material that does not show any adsorption of phenylephrine thereby causing no loss of potency and/or assay percentage during preparation, sterilization and during storage. In some aspects, the multilayer film may comprise other layers that may be made up of materials such as polyethylene, polypropylene, modified polyolefin-polyethylene polymers, styrene-polyolefin based polymers and block co-polymers thereof etc. In some aspects, the film may be an M312 film, such as Nexcel brand M312A film manufactured by SealedAir Corporation; an M315 film manufactured by SealedAir Corporation; an APP-series film manufactured by Polycine, such as APP-114S film manufactured by Polycine; a polypropylene film manufactured by Technoflex, such as an Inerta® film* manufactured by Technoflex; a cycloolefin polymer with a middle layer made up of linear low density polyethylene polymer and an outer layer made up of low density polyethylene polymer manufactured by Hosokawa; an Inerta 103 film, made up of an outer layer of polypropylene polymer with styrene-ethylene-butylene (SEB) block copolymer and a middle and inner layer made up of polypropylene based polyolefin polymer with styrene-ethylene butylene block copolymer, manufactured by Technoflex; or another commercially-available polymer film designed for use in intravenous bag products. In certain aspects, other polymers that are stable, with low leachables, and without physical deformation during terminal sterilization may also be used for the infusion bag.

Figure 4:
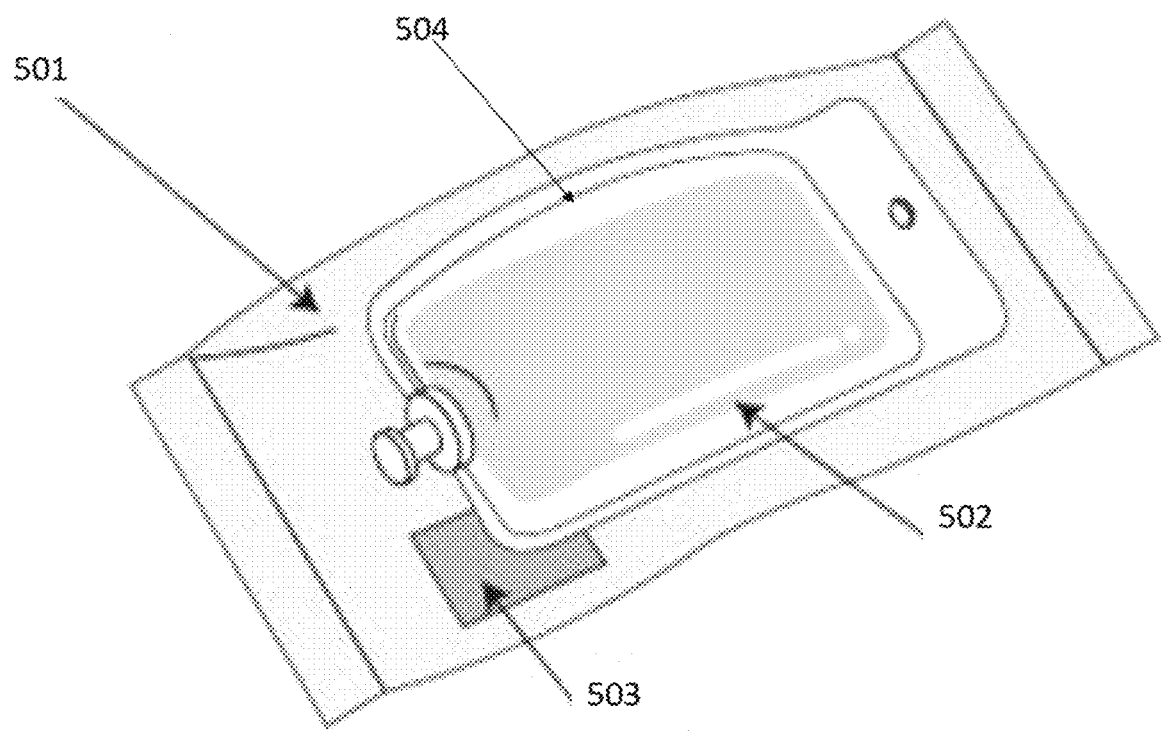
FIG. 4 shows an exemplary final packaging configuration for the phenylephrine product of the present disclosure wherein 501 indicates the overwrap; 502 indicates the phenylephrine solution; 503 indicates the oxygen absorber, and oxygen indicator; and 504 indicates the IV bag.
Figure 5:
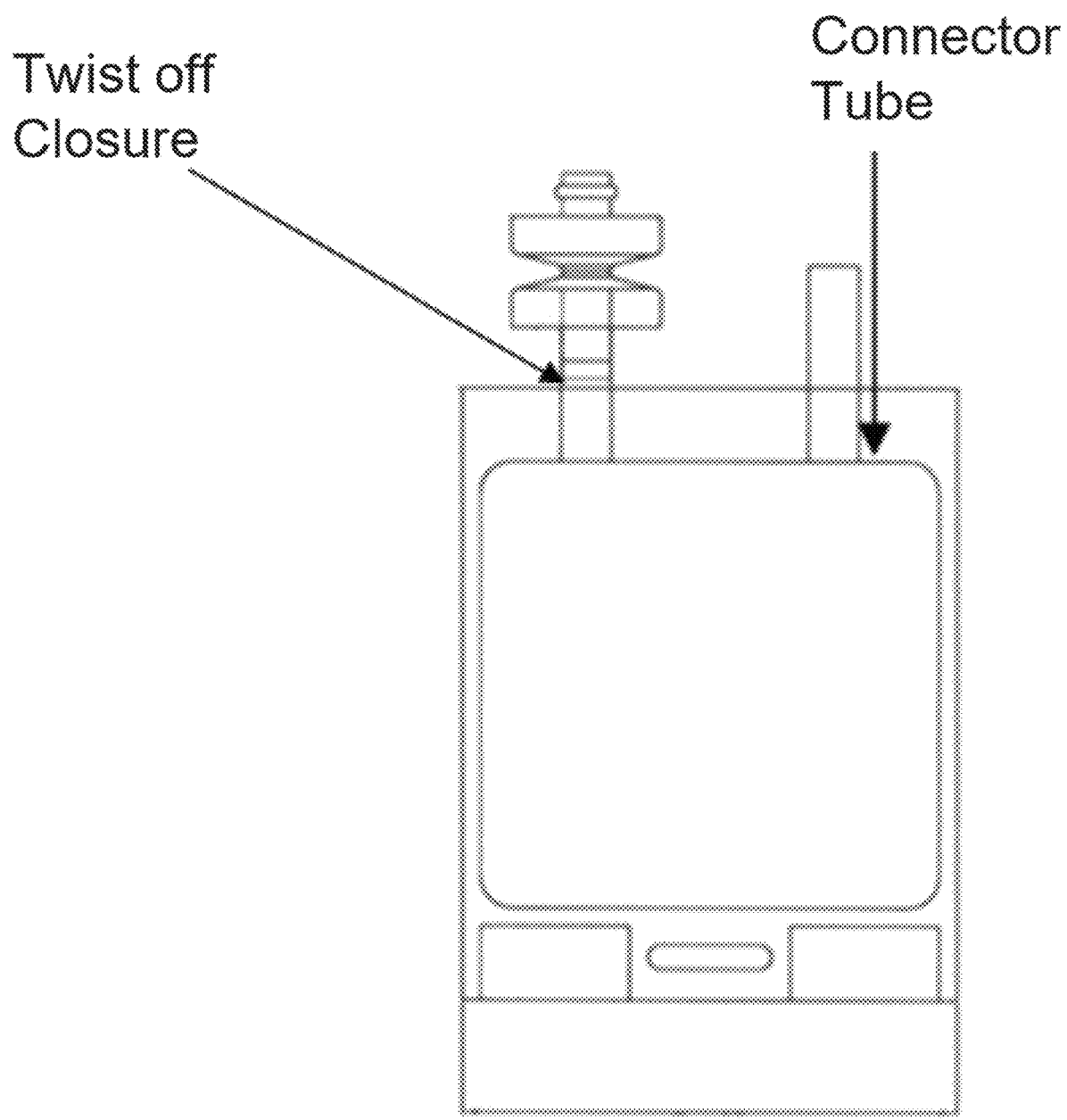
FIG. 5 shows a diagram of an exemplary primary packaging configuration of the present disclosure.

In some aspects, the infusion bag further comprises an overwrap. In some aspects, the overwrap comprises polyester, aluminum, polypropylene, or a combination thereof. In some aspects the infusion bag further comprises an oxygen absorber and oxygen indicator. In some aspects, the overwrap comprises a transparent strip over the oxygen indicator to allow for reading the oxygen indicator without removing the overwrap. For example as shown in FIG. 4, the solution of the phenylephrine or a pharmaceutically salt thereof (502) is disposed in a bag (504), which is packaged in a secondary packaging (501) containing an oxygen absorber and oxygen indicator (503). In some aspects, an oxygen indicator inside the secondary packaging (501) will show a first color to reflect acceptable oxygen levels, e.g., less than or <1 ppm and will show a second color to reflect that the oxygen has exceeded acceptable oxygen levels, e.g., greater than 0.5% or 1 ppm. In some aspects, the oxygen absorber is a treated iron powder. In some aspects, the oxygen indicator includes a self-adhesive label made of a laminated polyester/polypropylene complex containing an oxygen sensitive gel supported on a silicone PET.

In one aspect, the phenylephrine or a pharmaceutically salt thereof is chemically stable for at least 24 months when packaged with oxygen absorber and stored at a controlled room temperature. In one aspect, the controlled room temperature is 15-30° C. In one aspect, the controlled room temperature is 15-30° C.

In one aspect, the average number of particles equal to or greater than 10 µm present in the units tested does not exceed 6000 per 250 mL infusion bag when the phenylephrine product of the present disclosure comprising an aqueous phenylephrine solution is at room temperature for at least 24 months. In certain aspects, the average number of particles equal to or greater than 10 µm present in the phenylephrine product of the present disclosure units tested does not exceed 600 per container. In certain, the average number of particles equal to or greater than 10 µm present in the phenylephrine product of the present disclosure units tested does not exceed 60 per container. In one aspect, the average number of particles equal to or greater than 25 μm present in the units tested does not exceed 600 per 250 mL infusion bag when the phenylephrine product of the present disclosure is at room temperature for at least 24 months. In one aspect, the average number of particles equal to or greater than 25 μm present in the units tested does not exceed 60 per 250 mL infusion bag when the phenylephrine product of the present disclosure is at room temperature for at least 24 months.

In one aspect, the oxygen content after accelerated stability at 40° C.±2° C./15% RH±5% for 6 months is about 0.80 mcg/ml. In one aspect, the pH after accelerated stability at 40° C.±2° C./15% RH±5% for 6 months is about 3 to 6.5. In one aspect, the osmolality after accelerated stability at 40° C.±2° C./15% RH±5% for 6 months is about 270-320 mOsmol/kg. In one aspect, the total impurities after accelerated stability at 40° C.±2° C./15% RH±5% for 6 months is less than 0.5%.

In one aspect, the infusion bag is aseptically filled with the phenylephrine solution.

In one aspect, the disclosure provides a method of preparing the phenylephrine product of the present disclosure, comprising: (i) adding phenylephrine or a pharmaceutically salt thereof and one or more buffering agents to water; (ii) adjusting the pH to about 3 to 6.5 using a pH adjusting agent; (iii) adjusting the tonicity of the solution with a tonicity adjusting agent; (iv) filtering the solution of step (iii) in a first sterilizing filtration; (v) filtering the solution of step (iv) in a second sterilizing filtration; (vi) filling the solution into a sterile infusion bag; (vii) sealing the infusion bag of step (vi); (viii) overwrapping the sealed infusion bag of step (vii) wherein said overwrap comprises an overwrap, an oxygen absorber, and an oxygen indicator.

In one aspect, the disclosure provides a method of increasing blood pressure in a patient in need thereof, comprising administering the phenylephrine product of the present disclosure comprising an aqueous phenylephrine solution to the subject; and wherein the phenylephrine is administered as a continuous infusion. In one aspect, the phenylephrine solution is administered by an intravenous infusion. In one aspect, the phenylephrine is phenylephrine HCl administered at 0.5 mcg/kg/min to 1.4 mcg/kg/min, titrated to effect. In one aspect, the phenylephrine is phenylephrine HCl administered at 0.5 mcg/kg/minute to 6 mcg/kg/min, titrated to effect.

In one aspect, the disclosure provides a method of increasing blood pressure in a patient in need thereof, comprising administering the phenylephrine solution using the phenylephrine product of the present disclosure to the subject; and wherein the phenylephrine is administered as an intravenous bolus infusion. In one aspect, 50 mcg to 250 mcg of phenylephrine HCl, or an equivalent amount of phenylephrine as the free base or another pharmaceutically acceptable salt thereof, is administered.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the present disclosure and how to make and use them.

As used herein, the term "phenylephrine" refers to s benzene methanol, 3-hydroxy-α [(methyl amino) methyl]-hydrochloride (R) as the free base or pharmaceutically acceptable salt.

A pharmaceutically acceptable salt of phenylephrine can include, for example, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. In certain embodiments, the phenylephrine salt is phenylephrine HCl. In other non-limiting embodiments, phenylephrine comprises the structure depicted below:

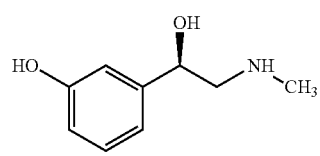

The term, "chemically stable," as used herein, refers to a chemical compound which retains its chemical structure and useful properties on a timescale of its expected usefulness. Specifically, the usefulness of the compound is maintained in the environment in which it is stored. Conversely, a compound lacks chemical stability if it decomposes under the conditions of a specific environment. As used herein in certain embodiments, "chemically stable" may mean resistant to degradation of phenylephrine into its known or unknown decomposition elements. The level of phenylephrine identified impurity that is acceptable can be up to 0.15% of the formulation as per the ICH guidelines for shelf-life determination, but in certain preferred embodiments, the amount of impurities is lower, e.g., less than 0.05% of the formulation.

As used herein, the terms "premix", "premixed", or "premixture" refers to a pharmaceutical formulation that does not require reconstitution or dilution prior to administration to a patient. For example, in contrast to non-premixed formulations of phenylephrine, the premixed compositions provided herein are suitable for administration to a patient without dilution by, for example, a clinician, hospital personnel, caretaker, patient or any other individual.

As used herein, the term "ready-to-use" refers to premixed compositions that are suitable for administration to a patient without further manipulation (e.g., a pharmaceutical formulation that is in the container from which the product is administered to the patient (such as an infusion bag or prefilled syringe) and does not require dilution or admixing before administration).

As used herein, the term "container closure system" refers to the sum of packaging components that together contain and protect the dosage form, including primary packaging components and secondary packaging components.

As used herein, the terms "primary packaging components" and "primary packaging" mean packaging components that are or may be in direct contact with the dosage form. For example, the primary packaging may be an infusion bag, including a flexible film component, one or more ports, and a closure system.

The terms "infusion bag," "intravenous bag," and "IV bag" may be used interchangeably herein and refer to a type of primary packaging, which comprises a bag film, port(s) and closure system(s). Such infusion bags may be used to administer intravenous infusion products.

The term "infusion container" as used herein refers to a type of primary packaging used to administer intravenous infusion products, for example, an infusion bag, a semi-flexible plastic infusion container, a prefilled syringe, a glass infusion container, etc.

As used herein, the term "flexible" refers to a material that has the ability to deform and return to its original shape when the applied stress is removed without breaking or damage at around standard temperature and pressure (STP), for example about 0° C.±40° C. and 1 atm±0.005 atm. Flexible materials are distinguished from rigid materials such as glass. A "flexible" infusion bag allows fluid to drain out of the bag without venting. A "flexible" infusion bag may have port tubes and/or closures that are made of rigid or semi-rigid materials, provided that the bag film is flexible.

As used herein, the terms "secondary packaging components" and "overwrap" refer to a packaging component that is intended to provide additional protection to the drug product but is not typically in direct contact with the dosage form during storage.

As used herein, the terms "subject" or "patient" refer to a human, a non-human mammal or a non-human animal. The compounds and compositions of the present disclosure have application in veterinary medicine as well as for humans, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

As used herein, the terms "pharmaceutical composition" or "pharmaceutical formulation" relates to compositions that can be formulated using one or more pharmaceutically acceptable diluents or excipients. A "pharmaceutically acceptable" solvent, diluent or excipient, as used herein, means approved by a regulatory agency of a federal or a state government, or as listed in the U.S. Pharmacopoeia or other generally recognized pharmacopoeia for use in mammals, and more particularly in humans.

As used herein, the term "titrated to effect" refers to a method of limiting potential side effects of a drug by administering the smallest dosage needed to obtain the desired effects in a patient, which can be readily determined according to standard good medical practice by those of skill in the art. In a non-limiting embodiment, a medication is titrated to effect by starting a medication at a low dose and slowly increasing the dose until the maximum effective dose is achieved or until side effects occur.

As used herein, the terms "about" and "approximately" as used herein means within an acceptable error range for the particular value as determined by one of ordinary skill in the art, which will depend in part on how the value is measured or determined, i.e., the limitations of the measurement system. In certain aspects, "about" can mean a range of up to 10% of a given value.

As used herein, the terms "aseptically filled" and "aseptic processing" refers to sterile filtration and aseptic processing of the premixed phenylephrine solution of the disclosure, wherein the pre-filtration followed by sterile filtration is used for sterilization of solution. For example, aseptic filling can be achieved by filtering the premixed phenylephrine solution of the disclosure through a pre-filter with a filter absolute rating: 0.45 µm followed by a filtration through two sterilizing filters (0.2 µm pore size filters) under aseptic conditions. The filtration can be pressure driven (conducted under compressed air) and the product solution can be aseptically filled into presterilized bag in line with filtration. After filling, port of the IV bags used for product solution filling can be sealed, e.g., thermally sealed.

As used herein, the terms "port," "tubing port," "port tube," and "connector tubing" refer to a connector which is sealed into the container portion of an infusion bag. An infusion bag may include one or more ports. The ports may include administrative and/or additive ports. The ports of the invention use commercially available polymers, elastomers, etc. and can comprise one or more layers. The ports may be coextruded.

As used herein, the term "closure" refers to a component that closes or seals a container. A closure provides an effective barrier against microbial contamination. In some aspects, the closure is a twist-off closure. The closures referred to herein may comprise commercially available polymers, elastomers, etc. and can comprise one or more layers.

As used herein, singular forms, including the singular forms "a" "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or".

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Pharmaceutical Formulations

The compounds and compositions of the invention may be formulated as pharmaceutical compositions by admixture with pharmaceutically acceptable solvents and excipients. For example, suitable components of pharmaceutical compositions are described in, for example, "Remington's Pharmaceutical Sciences" by Philip P. Gerbino, 21st Edition (or previous editions). In certain non-limiting embodiments, the compounds or compositions are provided in a therapeutically effective amount to an animal, such as a mammal, preferably a human, in need of treatment therewith, e.g., for treatment of hypotension resulting primarily from vasodilation. In some aspects, the compositions of the present disclosure are used in settings such as septic shock or anesthesia.

In certain non-limiting embodiments, phenylephrine is formulated as a pharmaceutical composition, wherein the phenylephrine is the only biologically active ingredient present in the composition. In another non-limiting embodiments, phenylephrine is formulated as a pharmaceutical composition, wherein the phenylephrine is formulated in combination with at least one or more other biologically active ingredients. The formulation is suitable for parenteral administration, such as intravenous, subcutaneous, intramuscular and intraperitoneal administration.

The pharmaceutical formulations suitable for injectable use, such as, for example, intravenous administration, include sterile aqueous solutions or dispersions and sterile powders for the extemporaneous preparation of sterile injectable solutions or dispersion. The pharmaceutical formulations can be stable under the conditions of manufacture and storage and can be preserved against the contaminating action of microorganisms such as bacteria and fungi. Solvents or dispersion mediums suitable for stable pharmaceutical formulations include, for example, water for injection (WFI), saline, aqueous dextrose, ethanol, polyol (for example, glycerol, propylene glycol, and polyethylene glycol, and the like), suitable mixtures thereof, and oils. In certain aspects, the solvent may be sterile WFI, 0.9% sodium chloride injection (normal saline), or 5% dextrose in water.

Pharmaceutical formulations may include tonicity adjusting agents, for example, sugars or water-soluble inorganic salts including but not limited to dextrose, glycerin, glycerol, mannitol, sorbitol, lactose, trehalose, potassium chloride, sodium chloride, sodium sulfate, sodium citrate, and combinations thereof. Sterile injectable solutions may be prepared by incorporating the phenylephrine in the required amounts in the appropriate solvent with various of the other ingredients enumerated above, as required, followed by filter sterilization.

Pharmaceutical formulations may include one or more excipients. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. The term "stabilizer" refers to a compound optionally used in the pharmaceutical compositions of the present invention in order to increase storage life.

In some aspects, formulations of the present disclosure are antioxidant-free. Non-limiting examples of antioxidants include histamine, methionine, ascorbic acid, sodium ascorbate, glutathione, vitamin E, vitamin C, poly(ethylenimine), N-acetyl cysteine, S-adenosylmethionine, sodium metabisulfite, propyl gallate, alpha-tocopherol, or a combination thereof. Thus, in some aspects, formulations of the present disclosure do not contain one or more antioxidants. For example, formulations of the present disclosure may be free of sulfites and/or metabisulfites.

Buffer systems for use with the formulations include citrate; acetate; bicarbonate; and phosphate buffers.

Pharmaceutical formulations may include one or more non-ionic surfactants. Examples of non-ionic surfactants include polysorbate 20, polysorbate 80, Triton™ X-100 (t-Octylphenoxypolyethoxyethanol, Polyethylene glycol tert-octylphenyl ether), Triton™ X-114 ((1,1,3,3-Tetramethylbutyl)phenyl-polyethylene glycol, Polyethylene glycol tert-octylphenyl ether), Nonidet™ P-40 (4-Nonylphenyl-polyethylene glycol, Imbentin-N/52, NP 40), Octyl α-glucoside, Octyl β-glucoside, Brij® 35 (Polyoxyethylene lauryl ether), Pluronic™ (Non-ionic copolymer surfactant).

Methods of Using Ready-to-Use Phenylephrine Compositions

As noted above, exemplary methods of treatment according to the disclosure include treatment of clinically important hypotension resulting primarily from vasodilation in the setting of anesthesia in a patient in need thereof comprising administration of phenylephrine to the patient, wherein the phenylephrine is administered in an amount effective to produce the desired effect.

The phenylephrine for use in the invention can be administered via any suitable route, including parenteral and intravenous routes. In a non-limiting embodiment, the therapeutic compound can be delivered in a controlled or sustained release system. For example, a compound or composition may be administered using intravenous infusion, continuous infusion, or other modes of administration. In certain non-limiting embodiments, the dosage of phenylephrine can be individualized and titrated to the desired clinical effect.

The present disclosure includes the following non-limiting list of items:

1. A phenylephrine product comprising an aqueous phenylephrine solution comprising phenylephrine or a pharmaceutically acceptable salt thereof, a tonicity adjusting agent, at least one pH adjusting agent, at least one buffering agent and water for injection, wherein the phenylephrine solution does not contain sodium metabisulfite or a chelating agent, wherein the phenylephrine product is sterile and ready-to-use.
2. The phenylephrine product of item 1, wherein the pharmaceutically acceptable salt is phenylephrine hydrochloride, and wherein the phenylephrine hydrochloride is at a concentration of about 0.05 to about 0.5 mg/ml and wherein the phenylephrine solution has oxygen content of <1 ppm.
3. The phenylephrine product of item 2, wherein the phenylephrine hydrochloride is at a concentration selected from a group consisting of about 0.08 mg/ml, about 0.2 mg/ml, and about 0.4 mg/ml.
4. The phenylephrine product of any preceding item, wherein the tonicity adjusting agent comprises sodium chloride, dextrose, glycerin, glycerol, mannitol, sorbitol, lactose, trehalose, potassium chloride, or a combination thereof.
5. The phenylephrine product of any preceding item, wherein the buffering agents comprise sodium citrate dihydrate, and citric acid monohydrate.
6. The phenylephrine product of any preceding item, wherein the buffering agents comprise sodium citrate dihydrate, and citric acid anhydrous.
7. The phenylephrine product of item 5 or item 6, wherein the sodium citrate dihydrate is at a concentration of from 0.05 to 0.5 mg/ml, optionally wherein the concentration is selected from the group 0.08 mg/ml, 0.2 mg/ml and 0.4 mg/ml.
8. The phenylephrine product of item 5 or item 7, wherein the citric acid monohydrate is at a concentration of from 0.05 to 0.05 mg/ml, optionally wherein the concentration is selected from the group 0.032 mg/ml, 0.25 mg/ml and 0.4 mg/ml.
9. The phenylephrine product of any one of items 6-7, wherein the citric acid anhydrous is at a concentration of from 0.008 to 0.05 mg/ml, optionally wherein the concentration is selected from the group 0.007 mg/ml, 0.18 mg/ml and 0.036 mg/ml.
10. The phenylephrine product of any preceding item, wherein the pH adjusting agent comprises hydrochloric acid, sodium hydroxide, or a combination thereof.
11. The phenylephrine product of any preceding item, wherein the pH of the phenylephrine solution is about 3 to about 6.5.
12. The phenylephrine product of any preceding item, wherein the phenylephrine solution is antioxidant-free.
13. The phenylephrine product of any preceding item, wherein the phenylephrine solution is free of a chelating agent, free of a preservative, and/or free of a complexing agent.

14. The phenylephrine product of any preceding item, wherein the phenylephrine solution has an osmolality of about 270-320 mOsmol/kg.
15. The phenylephrine product of any preceding item, wherein the amount of bacterial endotoxin inside the phenylephrine solution is 25 EU/mg or less.
16. The phenylephrine product of any preceding item, wherein phenylephrine solution is formulated as a total volume of about 100 to about 500 ml or about 250 ml.
17. The phenylephrine product of any preceding item, wherein the phenylephrine solution is contained in an infusion bag comprising at least one port.
18. The phenylephrine product of item 17, wherein the infusion bag comprises three ports.
19. The phenylephrine product of any one of items 17-18, wherein the infusion bag comprises at least one port closed with a closure.
20. The phenylephrine product of item 19, wherein the closure is composed of a plastic material.
21. The phenylephrine product of any one of items 19-20, wherein the closure is a twist-off closure.
22. The phenylephrine product of item 21, wherein the twist-off closure comprises polyethylene LDPE, polypropylene PP or a combination thereof.
23. The phenylephrine product of any one of items 17-22, wherein at least one port is a tubing port.
24. The phenylephrine product of any one of items 17-22, wherein two ports are tubing ports.
25. The phenylephrine product of any one of items 23-24, wherein the tubing port is used to fill the bag with the phenylephrine solution.
26. The phenylephrine product of any one of items 23-25, wherein the tubing port comprises a PP/EVA material.
27. The phenylephrine product of any one of items 23-26, wherein the tubing port comprises multi-layer co-extruded plastic connector tubing.
28. The phenylephrine product of any one of items 23-27, wherein the tubing port is PVC and plasticizer free.
29. The phenylephrine product of any one of items 23-28, wherein the tubing port is sealed.
30. The phenylephrine product of any one of items 23-29, wherein the tubing port is thermally sealed.
31. The phenylephrine product of any one of items 17-30, wherein the infusion bag comprises a flexible film.
32. The phenylephrine product of any one of items 17-31, wherein the infusion bag comprises a flexible polyolefin film.
33. The phenylephrine product of any one of items 17-32, wherein the infusion bag comprises a flexible multi-layer film.
34. The phenylephrine product of any one of items 17-32, wherein the infusion bag comprises a single layer of flexible film.
35. The phenylephrine product of any one of items 17-33, wherein the infusion bag comprises a flexible multi-layer film comprising an innermost layer comprising a material that does not show any adsorption of phenylephrine.
36. The phenylephrine product of any one of items 17-35, wherein the infusion bag comprises a flexible multi-layer film comprising polyolefin, polyethylene, polypropylene, modified polyolefin-polyethylene polymers, styrene-polyolefin based polymers, block copolymers, or any combination thereof.
37. The phenylephrine product of any one of items 17-36, wherein the infusion bag comprises 2 to 7 layers of flexible polyolefin film.
38. The phenylephrine product of any one of items 17-37, wherein the infusion bag comprises a flexible 5 layer polyolefin film.
39. The phenylephrine product of any one of items 17-38, wherein the infusion bag comprises an internal layer comprising of ethylene vinyl acetate.
40. The phenylephrine product of any one of items 17-39, wherein the infusion bag further comprises an overwrap.
41. The phenylephrine product of item 40, wherein the overwrap comprises polyester, aluminum, polypropylene, or a combination thereof, wherein the overwrap optionally comprises a transparent strip.
42. The phenylephrine product of any one of items 40-41, wherein the overwrap comprises four layers of formable film.
43. The phenylephrine product of any one of items 17-42, wherein the infusion bag further comprises an oxygen absorber and an oxygen indicator.
44. The phenylephrine product of item 43, wherein the oxygen absorber is an oxygen scavenger.
45. The phenylephrine product of any preceding item, wherein the phenylephrine or a pharmaceutically salt thereof is chemically stable for at least 24 months when packaged with an oxygen absorber and stored at a controlled room temperature.
46. The phenylephrine product of item 45, wherein the controlled room temperature is 15-30° C.
47. The phenylephrine product of any one of items 45-46, wherein the controlled room temperature is 15-30° C. with relative humidity (RH) at about 40%±5%.
48. The phenylephrine product of any preceding item, wherein the average number of particles equal to or greater than 10 µm present in the units tested does not exceed 600 per ready-to-use container when the container comprising a phenylephrine solution is stored at room temperature for at least 24 months.
49. The phenylephrine product of any preceding item, wherein the average number of particles equal to or greater than 25 µm present in the units tested does not exceed 60 per ready-to-use container when the container comprising a phenylephrine solution is stored at room temperature for at least 24 months.
50. The phenylephrine product of any preceding item, wherein the oxygen content after accelerated stability at 40° C.±2° C./15% RH±5% for 6 months is less than 1 ppm.
51. The phenylephrine product of any preceding item, wherein the pH after accelerated stability at 40° C.±2° C./15% RH±5% for 6 months is about 3 to 6.5.
52. The phenylephrine product of any preceding item, wherein the osmolality after accelerated stability at 40° C.±2° C./15% RH±5% for 6 months is about 270-320 mOsmol/kg.
53. The phenylephrine product of any preceding item, wherein the total impurities after accelerated stability at 40° C.±2° C./15% RH±5% for 6 months is less than 0.5%.
54. The phenylephrine product of any preceding item, wherein the phenylephrine product is free of sulfite- or bisulfite-containing compounds.
55. The phenylephrine product of any preceding item, wherein the phenylephrine product is antioxidant-free.
56. The phenylephrine product of any preceding item, wherein the phenylephrine product does not affect prothrombin time (PT), activated partial thromboplastin time (APTT) and Clauss fibrinogen (FibC) of human blood cells compared to human blood cells not contacted by the phenylephrine product.

57. The phenylephrine product of any preceding item, wherein the phenylephrine product does not cause increased hemolysis of human platelets compared to human platelets not contacted by the phenylephrine product.

58. The phenylephrine product of any one of items 17-57, wherein the infusion bag is an aseptically-filled infusion bag.

59. A method of preparing a phenylephrine product, comprising:
   i) introducing a sterile infusion bag into an aseptic environment;
   ii) introducing a sterile phenylephrine solution into an aseptic environment;
   iii) filling the sterile infusion bag with the sterile phenylephrine solution in the aseptic environment to produce an aseptically-filled infusion bag;
   iv) sealing the filled infusion bag in the aseptic environment; and
   v) adding an oxygen absorber and an oxygen indicator;
   vi) overwrapping the sealed infusion bag.

60. The method of item 59, wherein the phenylephrine solution comprises about 0.05 to about 0.5 mg/ml phenylephrine or pharmaceutically acceptable salt thereof, a tonicity adjusting agent, at least one pH adjusting agent, at least one buffering agent and water for injection.

61. The method of item 59 or item 60, wherein the pharmaceutically acceptable salt is phenylephrine hydrochloride.

62. The method of any one of items 59-61, wherein the tonicity adjustment agent comprises sodium chloride, dextrose, glycerin, glycerol, mannitol, sorbitol, lactose, trehalose, potassium chloride, or a combination thereof.

63. The method of any one of items 59-62, wherein the buffering agents are sodium citrate dihydrate and citric acid monohydrate.

64. The method of any one of items 59-63, wherein the buffering agents are citrate dihydrate and citric acid anhydrous.

65. The method of any one of items 59-64, wherein the pH adjusting agents comprise hydrochloric acid, sodium hydroxide, or a combination thereof.

66. The method of any one of items 59-65, wherein the method further comprises the step of producing the sterile phenylephrine solution by filtering a phenylephrine solution through one or more in-line sterile filters having a pore size of 0.22 micron or less.

67. The method of any one of items 59-66, wherein the method further comprises the step of producing the sterile phenylephrine solution by filtering a phenylephrine solution through two in-line sterile filters having a pore size of 0.22 micron or less.

68. The method of any one of items 59-67, wherein the infusion bag comprises a bag comprising a flexible multilayer polyolefin film, at least one port, and at least one port closed with a twist-off closure.

69. The method of any one of items 59-69, wherein the infusion bag comprises three ports.

70. The method of any one of items 68-69, wherein the twist-off closure comprises polyethylene LDPE, polypropylene PP or a combination thereof.

71. The method of any one of items 69-70, wherein at least one port is a tubing port.

72. The method of any one of items 69-71, wherein the infusion bag comprises two ports that are tubing ports.

73. The method of any one of items 71-72, comprising filling the infusion bag with the phenylephrine solution via a tubing port.

74. The method of any one of items 72-73, wherein at least one tubing port comprises a PP/EVA material.

75. The method of any one of items 72-74, wherein at least one tubing port comprises multi-layer co-extruded connector tubing.

76. The method of any one of items 72-75, wherein at least one tubing port is thermally sealed.

77. The method of any one of items 59-76, wherein the overwrapping step comprises overwrapping the sealed infusion bag with an overwrap comprising polyester, aluminum, polypropylene, or a combination thereof.

78. The method of any one of items 59-77, wherein the overwrap comprises four layers of formable film.

79. The method of any one of items 59-78, further comprising providing an oxygen absorber in the phenylephrine product.

80. The method of item 79, wherein the oxygen absorber comprises an oxygen scavenger and an oxygen indicator.

81. The method of any one of items 59-80, wherein preparing the sterile phenylephrine solution comprises the steps of:
   i) adding phenylephrine or a pharmaceutically salt thereof to water to obtain a phenylephrine solution;
   ii) adding one or more buffering agents to the phenylephrine solution of step i);
   iii) adjusting the pH of the phenylephrine solution of step ii) to about 3 to 6.5 using a pH adjusting agent;
   iv) adjusting the tonicity of the phenylephrine solution of step iii) with a tonicity adjusting agent;
   v) filtering the phenylephrine solution of step iv) in a first sterilizing filtration step;
   vi) filtering the phenylephrine solution of step v) in a second sterilizing filtration step to obtain a sterile phenylephrine solution;
   vii) aseptically filling the sterile phenylephrine solution of step vi) into a sterile infusion bag; and
   viii) sealing the sterile infusion bag of step vii) to obtain a sterile filled infusion bag.
   ix) adding an oxygen absorber and an oxygen indicator; and
   x) overwrapping the sterile infusion bag.

82. The method of item 81, wherein the sealing step comprises heat welding.

83. The method of any one of items 81-82, wherein the method does not include terminal sterilization.

84. The method of any one of items 59-83, wherein the method does not include autoclaving.

85. A method of increasing blood pressure in a patient in need thereof, comprising administering the aqueous phenylephrine solution via the phenylephrine product of any one of items 1-58 to the subject; and wherein the aqueous phenylephrine solution is administered as a continuous infusion.

86. The method of item 85, wherein the aqueous phenylephrine solution is administered by an intravenous infusion.

87. The method of any one of items 85-86, wherein the aqueous phenylephrine solution is phenylephrine hydrochloride administered at 0.5 mcg/kg/min to 1.4 mcg/kg/min.

88. The method of any one of items 85-86, wherein the aqueous phenylephrine solution is phenylephrine hydrochloride administered at 0.5 mcg/kg/min to 6 mcg/kg/min.

89. A method of increasing blood pressure in a patient in need thereof, comprising administering the aqueous phenylephrine solution via the phenylephrine product of any one of items 1-58 to the subject; and wherein the phenylephrine solution is administered as an intravenous bolus injection or infusion.

90. The method of item 85, wherein 50 mcg to 250 mcg of phenylephrine hydrochloride is administered as an intravenous bolus injection or infusion.

91. A method of for increasing blood pressure in adults with clinically important hypotension, wherein an aqueous phenylephrine solution comprising phenylephrine or a pharmaceutically acceptable salt thereof, a tonicity adjusting agent, at least one pH adjusting agent, at least one buffering agent and water for injection, wherein the phenylephrine solution does not contain sodium metabisulfite or a chelating agent, wherein the phenylephrine product is sterile and ready-to-use, wherein the phenylephrine solution has oxygen content of <1 ppm, wherein the phenylephrine product does not cause increased hemolysis of human platelets compared to human platelets not contacted by the phenylephrine product is administered at 8.64 mg/kg/day.

EXAMPLES

The following examples are merely illustrative of the presently disclosed subject matter and they should not be considered as limiting the scope of the present disclosure in any way.

Example 1: Exemplary Formulations

In certain non-limiting examples, phenylephrine formulations were made according to the compositions of Table 1. In some aspects, the amount per infusion bag of the inactive ingredients was about 0.9% (w/v) sodium chloride, 0.0008-0.0004% (w/v) citric acid monohydrate, 0.0032-0.016% (w/v) sodium citrate dihydrate, sodium hydroxide (q.s. to pH) and hydrochloric acid (q.s. to pH).

TABLE 1

Phenylephrine Hydrochloride in Sodium Chloride Product Formulations
Phenylephrine Hydrochloride in Sodium Chloride Formulation

| Components | | | |
|---|---|---|---|
| Phenylephrine HCl | 0.08 mg/ml | 0.2 mg/ml | 0.4 mg/ml |
| Sodium Citrate Dihydrate, USP | 0.032 mg/ml | 0.08 mg/ml | 0.16 mg/ml |

TABLE 1-continued

Phenylephrine Hydrochloride in Sodium Chloride Product Formulations
Phenylephrine Hydrochloride in Sodium Chloride Formulation

| Components | | | |
|---|---|---|---|
| Citric acid Monohydrate, USP | 0.008 mg/ml | 0.02 mg/ml | 0.04 mg/ml |
| (as Citric acid Anhydrous, USP) | 0.007 mg/ml | 0.018 mg/ml | 0.036 mg/ml |
| Sodium Chloride | 9 mg/ml | 9 mg/ml | 9 mg/ml |
| Water for Injection | q.s. to 1 mL | q.s. to 1 mL | q.s. to 1 mL |

The present disclosure includes additional phenylephrine products provided in different volumes with the same proportion of components as listed in Table 1 above. Further, the present disclosure includes other solvent systems may be substituted for the sodium chloride and water for injection. As one example, 5% dextrose in water for injection may be used in place of sodium chloride. Further the present disclosure includes use of phenylephrine as the free base or any pharmaceutically acceptable salt of phenylephrine; in such embodiments, the concentration of phenylephrine base is equivalent to the concentration of phenylephrine base in the phenylephrine HCl salt formulations disclosed herein. For example, 0.2 mg/mL of phenylephrine HCl is equivalent to 0.164 mg/mL of phenylephrine base. The phenylephrine formulations above beneficially do not require an antioxidant or added chelating agent such as edetate disodium (EDTA).

Example 2: Manufacturing Process

Process for Compounding of Bulk Solution

A phenylephrine product of the disclosure was produced in an aqueous solution and aseptically filled. The manufacturing process involved compounding a bulk solution. For compounding of bulk solution, predefined volume (90%) of Water for Injection (WFI) was collected in the compounding vessel prior start of the compounding. Temperature of WFI and temperature of solution throughout the compounding process was maintained in the range of ≤22° C. Mixing of the solution was achieved by recirculation of solution through the tri-blender system, with recirculation speed maintained at no less than 1.7 Us. First, dispensed quantity of Sodium Chloride, Sodium Citrate Dihydrate and Citric Acid was added. Then a dispensed quantity of phenylephrine hydrochloride previously dissolved was introduced into the vessel and Hydrochloric acid or sodium hydroxide was added for pH adjustment (if any). After pH was adjusted, batch weight made up to the predefined weight with WFI.

After batch weight make up solution was recirculated at a speed of no less than 1.7 Us and the samples were taken from the compounding vessel after 5, 10, and 15 minutes of recirculation and analyzed for appearance, pH, conductivity, density, assay and osmolality for six batches of the aqueous phenylephrine solution of the disclosure with the same proportion of components as listed in Table 1 as shown in Table 2 below.

TABLE 2

Dissolution data

| Parameter | Time point (min) | Requirements | Batch 1 | Batch 2 | Batch 3 | Batch 4 | Batch 5 | Batch 6 |
|---|---|---|---|---|---|---|---|---|
| Appearance | 5 | Clear, Colorless solution without visible particles | Comply | Comply | Comply | Comply | Comply | Comply |
| | 10 | | Comply | Comply | Comply | Comply | Comply | Comply |
| | 15 | | Comply | Comply | Comply | Comply | Comply | Comply |

TABLE 2-continued

Dissolution data

| Parameter | Time point (min) | Requirements | Batch 1 | Batch 2 | Batch 3 | Batch 4 | Batch 5 | Batch 6 |
|---|---|---|---|---|---|---|---|---|
| pH | 5 | 4.8-5.5 | 5.392 | 5.395 | 5.382 | 5.348 | 5.299 | 5.308 |
| (pH Units) | 10 | | 5.393 | 5.397 | 5.375 | 5.337 | 5.316 | 5.327 |
| | 15 | | 5.381 | 5.372 | 5.404 | 5.334 | 5.311 | 5.305 |
| Conductivity | 5 | For information | 15.29 | 15.59 | 15.39 | 15.48 | 15.26 | 15.59 |
| (mS/cm) | 10 | | 15.33 | 14.94 | 15.39 | 15.50 | 15.17 | 15.56 |
| | 15 | | 15.32 | 15.49 | 15.39 | 15.51 | 15.15 | 15.58 |
| Density (g/mL) | 10 | For information | 1.0033 | 1.003 | 1.0033 | 1.00347 | 1.0035 | 1.00348 |
| Assay (%) | 10 | 95.0-105.0 | 101.58 | 102.4 | 100.99 | 100.3 | 100.7 | 100.3 |
| Osmolality | 5 | 270-330 | 290 | 293 | 290 | 294 | 294 | 291 |
| (mOsmol/kg) | 10 | | 289 | 294 | 292 | 296 | 294 | 290 |
| | 15 | | 291 | 294 | 290 | 294 | 295 | 292 |

The results confirmed that all raw materials were completely dissolved and that the produced bulk solution was well mixed by recirculation.

Sterilization

The inventors found that terminal sterilization by autoclaving caused degradation of phenylephrine and significant increase in Leachables components. Therefore, the present disclosure includes producing a sterile product for parenteral use using aseptic conditions, through the filtration of the bulk solution on sterilizing filters (0.2 μm porosity filters) as shown in FIG. 1.

Batches of the phenylephrine composition of the present disclosure formulated as in Table 1 were manufactured for the study of the effect of autoclaving on product behavior by autoclaving at a target temperature T=121° C.±1° C. and time at different FOs according to USP <1222>, which is incorporated fully herein by reference.

The table below show the Critical Quality Attributes of the drug product. The objective of this study was to evaluate the quality of the proposed manufacturing process to determine whether the manufacturing process will endure the desired final product study.

TABLE 3

Critical Quality Attributes (COA) of the drug product

| Critical Quality Attributes (CQA) of Drug Product | Target |
|---|---|
| Appearance of solution | Clear, colorless, free from visible particles |
| pH | 3.0-6.5 |
| Assay | 90.0-110.0% of the labeled amount of phenylephrine hydrochloride |
| Degradation product | Not more than 1.3% |
| Osmolality | 270-330 mOsmol/kg |
| Sterility | Sterile |
| Microbial contamination/ Bacterial endotoxins/ Particulate matter | Meets the USP requirement |
| Residual solvent | Meets the requirements of USP option 2, which is fully incorporated herein |
| Elemental impurities | Meets the requirements of ICH Q3D, which is fully incorporated herein |
| Container content/ Uniformity of content | Not less than labeled volume |

The table below show the results of the autoclaving study using several batches of the phenylephrine hydrochloride product formulation of the disclosure, containing 0.08 mg/ml of phenylephrine HCL.

TABLE 4

Effect of autoclaving

| Batch # | Appearance Clarity/Color/ Foreign Matter | pH (pH units) | Osmolality (mOsmol/ Kg) | Assay (%) | Total Impurities (%) |
|---|---|---|---|---|---|
| RD004-15 Not sterilized | Clear/colorless/free from foreign matter | 5.2 | 295 | 99.2 | 0.10 |
| RD0004-15 Sterilized $F_0 15$ | Clear/colorless/free from foreign matter | 5.2 | 290 | 99.1 | 0.31 |
| RD004-15 Sterilized $F_0 20$ | Clear/colorless/free from foreign matter | 5.2 | 289 | 99.0 | 0.56 |
| RD0004-15 Sterilized $F_0 20x2$ | Clear/colorless/free from foreign matter | 5.2 | 292 | 98.8 | 0.93 |

Analysis of the impurities observed after autoclaving show an increase of impurities compared to a non-sterilized version of the same batch of the phenylephrine hydrochloride product formulation of the disclosure.

TABLE 5

Impurities resulting from autoclaving (limit <=0.02%)

| | Not sterilized RD004-15A | Sterilized $F_0 15$ RD004-15A | Sterilized $F_0 20$ RD004-15A | Sterilized $F_0 20x2$ RD004-15A |
|---|---|---|---|---|
| RRT 0.8 | — | 0.07 | 0.12 | 0.19 |
| RRT 0.9 | — | 0.17 | 0.37 | 0.51 |
| RRT 1.63 | 0.04 | 0.04 | — | 0.04 |

Figure 6:
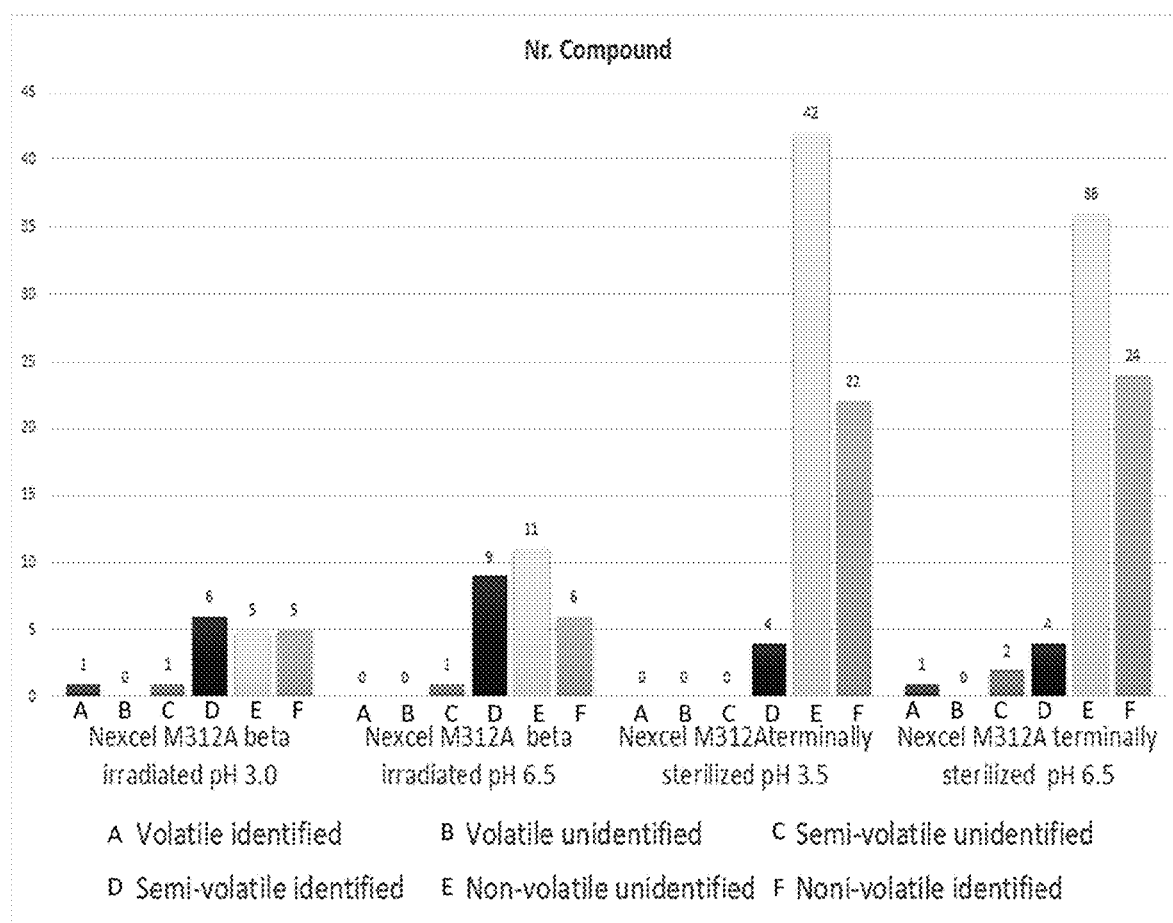
FIG. 6 shows a graph comparing the total leachables detected in the phenylephrine solution of the disclosure contained in an infusion bag after terminal sterilization or beta irradiation.

Furthermore, FIG. 6 and Table 6 show the difference of total leachables between terminally sterilized and beta irradiated phenylephrine solution in an infusion bag.

These results demonstrate that the phenylephrine composition of the present disclosure should not be terminally sterilized by autoclaving because an increase in impurities was noted in the characteristics of the phenylephrine solution (such as the phenylephrine assay, pH, etc.) after autoclaving. FIG. 6 shows the difference of total leachables between terminally sterilized and beta irradiated phenylephrine solution in an infusion bag.

TABLE 6

| NR. Of Detected Compound (AET 66 µg/m2) | | | | |
|---|---|---|---|---|
| | Nexcel M312A beta irradiated pH 3.0 | Nexcel M312A beta irradiated pH 6.5 | Nexcel M312A terminally sterilized pH 3.5 | Nexcel M312A terminally sterilized pH 6.5 |
| Volatile identified (Nr) | 1 | 0 | 0 | 1 |
| Volatile unidentified (Nr) | 0 | 0 | 0 | 0 |
| Semi-volatile unidentified (Nr) | 1 | 1 | 0 | 2 |
| Semi-volatile identified (Nr) | 6 | 9 | 4 | 4 |
| Non-volatile unidentified (Nr) | 5 | 11 | 42 | 36 |
| Noni-volatile identified (Nr) | 5 | 6 | 22 | 24 |

Sterilization Aseptic Filling:

To maintain sterility of the phenylephrine product of the disclosure, the bulk solution described above was introduced to the primary packaging using an aseptic filling technique. The phenylephrine product of the disclosure was filled in 300 mL bags equipped with two tubing ports and a port sealed with a twist-off closure. 300 mL infusion bags were made of a non-PVC-latex free material, a 5-layer, polyolefin based on co-extrude film. The connector tubing connecting each port to the bag was composed of Polypropylene/Ethyl-VinylAcetate (PP/EVA). The twist-off closure (spike port) was composed of polypropylene PP/polyethylene LDPE, and was PVC-free and plasticizer-free. Each infusion bag was over-wrapped with four layer formable film composed of Polyester/Aluminum/Polyester/Polypropylene.

The primary packaging and closure (PCC) represent the primary container that is in contact with the drug product and comprise the infusion bag and the ports. The PCC have a thermic sealed filling tube and a twist-off closure mounted. This twist-off closure is characterized by the presence of a membrane. The membrane creates a barrier, splitting the twist-off closure in two parts.

Aseptic filling of the phenylephrine bulk solution was carried out using an automatic filling machine Operators introduced sterile empty IV bags in a sealed triple polyethylene bag through a dedicated pass-box) into the material preparation room containing the filling machine, leaving the first external bag in the pass box. In the room, designated operators loaded the sterile empty bags into a sterilizer. The external surface was sterilized with a validated cycle Once bags were in the material preparation room they were protected from external environment by Laminar Air Flow (LAF). The assigned operator placed sterile empty bags in the loading position on the filling machine.

The filling machine automatically performed the following manufacturing steps:
1) took the sterile empty IV bags comprising at least one tubing port;
2) cut the tubing port to create an opening;
3) inserted the tubing port of the IV bag into filling nozzles;
4) filled each bag through the tubing port with the drug product solution until the target weight (volume); and
5) sealed the tubing port.

At the end of the filling step, the tubing port of each IV bag, which contained the drug product solution, was automatically sealed using heat welding at the selected temperature for the validated time by the filling machine.

Example 3: Filtration, Filling and IV Bag Sealing Studies

The ready-to-use, aseptically filled phenylephrine product of the present disclosure was manufactured using sterile filtration and aseptic processing of bulk solution, wherein pre-filtration followed by sterile filtration is used for sterilization of solution.

Compounded phenylephrine product solution batch was filtered through a pre-filter (filter absolute rating: 0.45 µm) followed by a filtration through two sterilizing filters (0.2 µm pore size filters). The filtration was pressure driven (conducted under compressed air) and the product solution was aseptically filled into pre-sterilized bag in line with filtration using the aseptic filling technique described above. After filling, port of the IV bags used for product solution filling were thermally sealed.

The potential adsorption of drug substance by the filter was evaluated using an assay after 72 hours; no significant change was detected for pH and osmolality value. Filter compatibility was performed for three concentrations (Phenylephrine 20 mg/250 ml, Phenylephrine 50 mg/250 ml, and Phenylephrine 100 mg/250 ml). All results were within acceptance criteria and consistent throughout the filling operation for each of nine manufactured product solution batches, confirming the bulk solution uniformity and filter compatibility throughout the process.

The aseptically filled infusion bag comprising an aqueous phenylephrine solution of the disclosure were overwrapped using polyester/aluminum/polyester/polypropylene overwrap and oxygen absorber and oxygen indicator was placed inside the overwrapping to prevent deterioration of drug product through oxidation pathways. The oxygen absorber and oxygen indicator, is placed on the aluminum film with the adhesive part of the absorber adhered to the film itself. IV bags are subsequently overwrapped using the polyester/aluminium/polyester/polypropylene overwrap. Appearance of overwrapped product and overwrap integrity, as well as presence of variable data, was checked for each overwrapped finished product.

A study was performed to evaluate the oxygen absorption capacity of the oxygen absorber. This was verified by monitoring the dissolved oxygen content (ppm) of 300 mL infusion bags filled with WFI and overwrapped with a polyester/aluminum/polyester/polypropylene overwrap.

TABLE 7

| Oxygen Data obtained at 25° C. (long term stability) | | | | |
|---|---|---|---|---|
| Time Station | Color of the Indicator | Oxygen Content | Change from T = 0 (ppm) | Change from T = 0 (%) |
| T = 0 | Yellow | 8.24 | — | — |
| T = 3 hours | Yellow | 6.64 | −1.60 | −19.4 |
| T = 6 hours | Yellow | 5.41 | −2.83 | −34.3 |
| T = 1 day | Yellow | 0.71 | −7.53 | −91.4 |
| T = 30 hours | Yellow | 0.56 | −7.68 | −93.2 |
| T = 2 days | Yellow | 0.51 | −7.73 | −98.3 |
| T = 1 week | Yellow | 0.14 | −8.10 | −98.3 |
| T = 1 month | Yellow | 0.13 | −8.11 | −98.4 |

Figure 2:
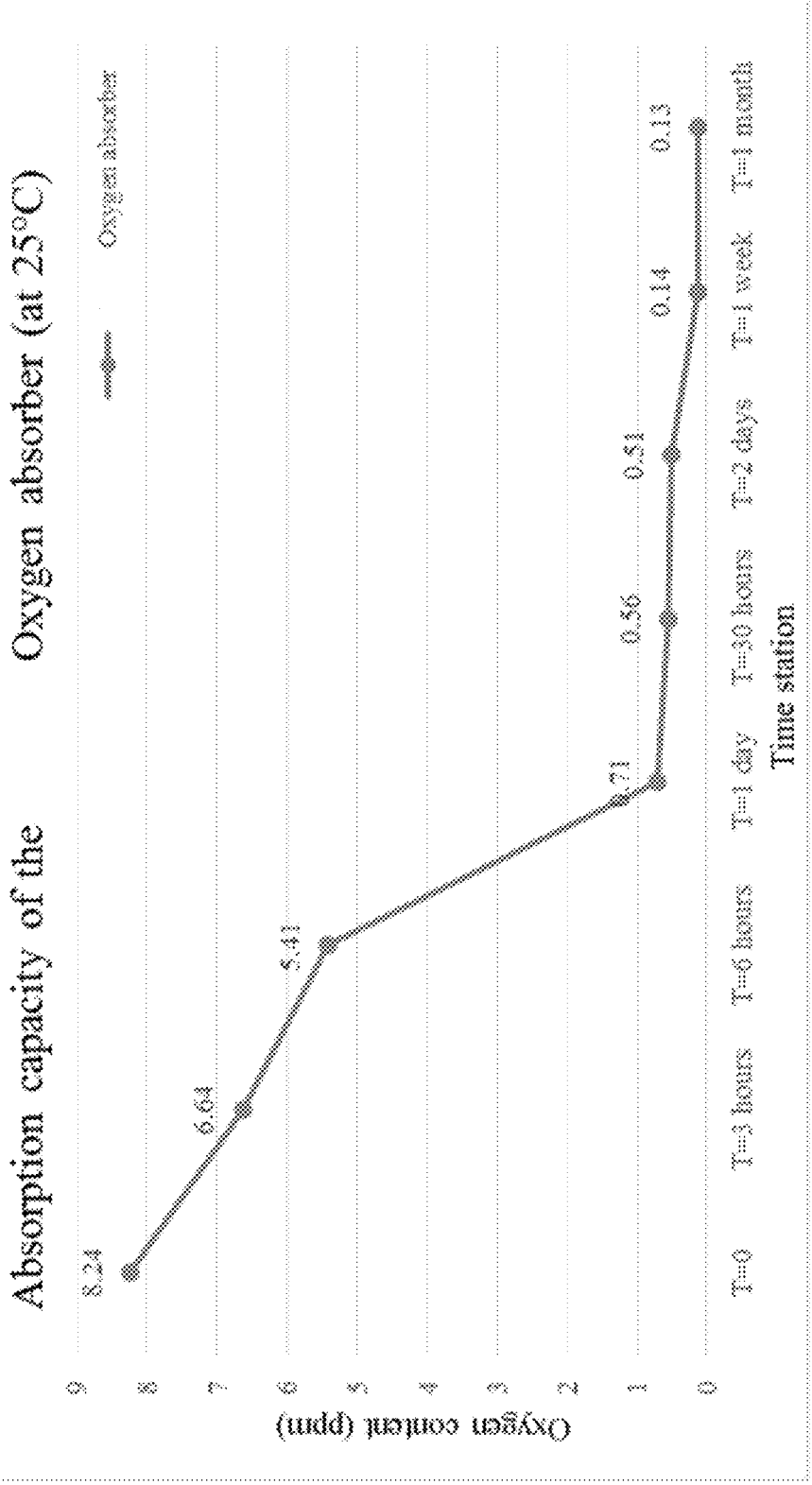
FIG. 2 shows the dissolved oxygen content at 25° C. in the presence of the oxygen absorber used in the phenylephrine product of the present disclosure over a period of 1 month.

After 2 days, the oxygen absorber made the tested environment sufficiently anoxic (about 0.5 ppm). The oxygen indicator did not change color (to blue) immediately after contact with oxygen but remained yellow since it is protected by overwrap. This means that the color change reaction did not take place in time in the short time when the dissolved oxygen remained around 5-8 ppm (6 hours). After one day, the absorber kept the anoxic environment and the color of the oxygen indicator remained yellow as can be seen in FIG. 2.

TABLE 8 oxygen results obtained at 40° C. (Accelerated stability results)

| Time Station | Color of the Indicator | Oxygen Content | Change from T = 0 (ppm) | Change from T = 0 (%) |
|---|---|---|---|---|
| T = 0 | Yellow | 8.24 | — | — |
| T = 3 hours | Yellow | 5.43 | −2.81 | −34.1 |
| T = 6 hours | Yellow | 3.13 | −5.11 | −62.0 |
| T = 1 day | Yellow | 0.86 | −7.38 | −89.6 |
| T = 30 hours | Yellow | 0.37 | −7.87 | −95.5 |
| T = 2 days | Yellow | 0.35 | −7.89 | −95.8 |
| T = 1 month | Dark Yellow | 0.24 | −8.00 | −97.1 |

Figure 3:
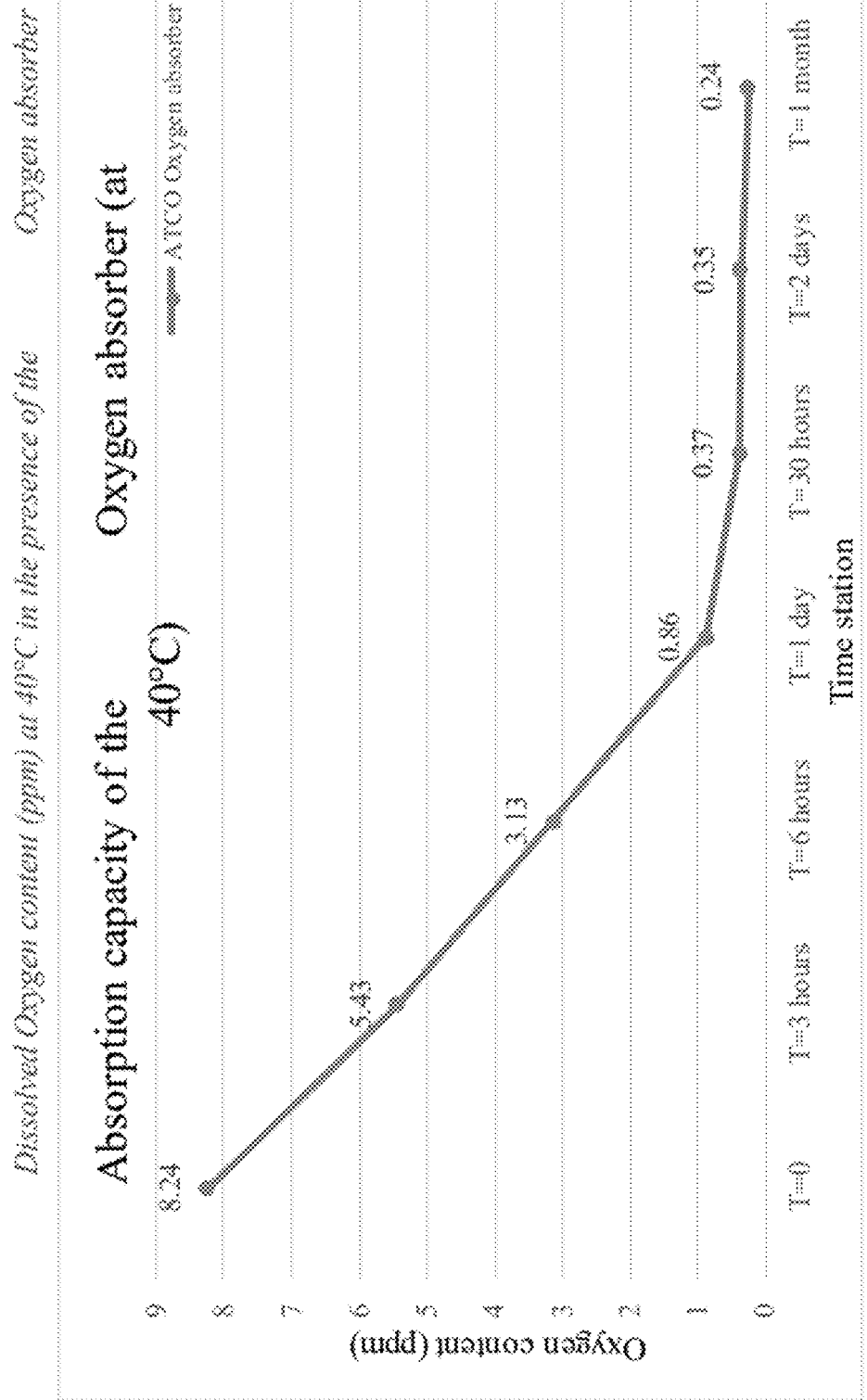
FIG. 3 shows the absorption capacity at 40° C. in the presence of the oxygen absorber used in the phenylephrine product of the present disclosure over a period of 1 month.

After 30 hours the oxygen absorber made the tested environment sufficiently anoxic (about 0.4 ppm). The acceptable level of anoxia was reached earlier than the bags stored at 25° C. The oxygen indicator did not change color immediately after contact with oxygen but remained yellow. This means that the color change reaction did not take place in time in the short time when the dissolved oxygen remains around 5-8 ppm (6 hours). After one month the absorber kept the anoxic environment but the oxygen indicator became slightly darker (dark yellow) as can be seen in FIG. 3.

In addition, a study was carried out to understand how long it took the indicator, if exposed to air, to become blue. Immediately after removing the indicator from its original packaging (under vacuum), the color of the indicator was bright yellow and after 24 hours it became dark yellow. The obvious color change occurred after 7 days (dark green). The reaction ended after 9 days (Blue).

A study was also performed to evaluate the ability of the oxygen absorbers to absorb oxygen when exposed to air for longer periods of time using an exemplary batch of the phenylephrine product of the disclosure. An oxygen absorber subjected to different periods of exposure to air was inserted between the infusion bag and the overwrap. The product was placed on stability at 25° C.±2° C./40%±5% RH (long-term condition) for 7 days and then the oxygen content was measured. Table 8 below shows the stability results of the oxygen absorber's holding time and power after air exposure and before use.

TABLE 9

Oxygen Absorber

| Sample | Number of bags analyzed | Absorber and indicator exposure time to air | Information about the Stability Conditions | Color of the indicator | Mean of the Oxygen content in solution (mg/L) |
|---|---|---|---|---|---|
| T = 0 * | — | — | — | Yellow | 8.35 |
| RD018-18 ** | 1 | 0 minutes | 7 days at 25° C. | Yellow | 0.14 |
| RD023-18A | 2 | 30 minutes | 7 days at 25° C. | Yellow | 0.25 |
| RD023-18B | 2 | 1 hour | 7 days at 25° C. | Yellow | 0.26 |
| RD023-18C | 2 | 1 hour and 30 minutes | 7 days at 25° C. | Yellow | 0.28 |
| RD023-18D | 2 | 2 hours | 7 days at 25° C. | Yellow | 0.33 |
| RD023-18E | 2 | 3 hours | 7 days at 25° C. | Yellow | 0.67 |

The results of the studies above demonstrate that the manufacturing process in accordance to the procedure shown in FIG. 1 is compatible with manufacturing the phenylephrine product of the invention as no significant change was noted in the characteristics of the phenylephrine solution (such as an increase in impurities, change in oxygen content, etc.) during the dissolution and sterilization steps till the oxygen absorber is used, after removal from its undervacuum packaging, within 3 hours.

Example 4: In Vitro Hemocompatibility Study

To test for hemocompatibility of the ready-to-use aseptically filled phenylephrine product of the present disclosure for intravenous administration at 0.4 mg/mL, the effect on platelet clumping and the effect on coagulation parameters in human citrated blood was tested to assess the product's hemolytic potential. The phenylephrine product used for this study had a phenylephrine hydrochloride concentration of 0.4 mg/mL with the same proportion of components as listed in Table 1 above. Previously, phenylephrine products used for intravenous administration are first diluted from a concentrated stock solution of 10 mg/ml to a concentration of 0.2 mg/ml of phenylephrine hydrochloride before the phenylephrine hydrochloride solution is used for continuous intravenous administration or 0.1 mg/ml for intravenous bolus administration. This study surprisingly shows that intravenous administration of the phenylephrine product of the present disclosure at 0.4 mg/ml does not significantly affect hemolytic potential compared to a negative control.

The procedure used for the hemolytic potential analysis was based on methods described in Prieur D J, et al, *Procedures for preclinical toxicologic evaluation of cancer,* 4 Cancer Chemother. Rep. 1-39 (1973) and modified to take account of the challenges outlined by Dal Negro G, et. al., *A new approach for evaluation of the in vitro haemolytic potential of a solution of a new medicine,* 6 Comp. Haematol. Int. 35-41. (1996), which are fully incorporated herein by reference. In summary, Prieur et. al. outlined the need to mix the highest concentration of a test formulation with whole blood for a hemolysis analysis to confirm that doses of the test product were compatible for the appropriate species to be dosed. Dal Negro, et. al. explained how to relate the static in vitro model to infusion rates and provided detailed methodology from which the study was designed.

Plasma compatibility was assessed by reviewing a number of parameters which could indicate incompatibility of the test item with plasma, including platelet clumping, coagulation parameters, and crystal formation in the whole blood.

The IV infusion rate used in this study was 1.2 mL/min. A peripheral venous flow rate of 8 mL per minute was assumed based on Dal Negro et. al. The ratio of blood to the 0.4 mg/mL formulation of the phenylephrine product of the present disclosure ("formulation") was calculated by dividing the IV infusion rate (ml/min) by the peripheral venous flow rate (ml/min), therefore, a ratio of 1:0.15 (blood: formulation) was used for this study. This ratio was tested for all formulations. Double the calculated ratio was also tested for safety reasons.

To determine the hematocrit (Hct), an aliquot of untreated whole blood from each pool was analyzed in triplicate on the Siemens Advia 120.

The hemolytic potential was analyzed by collecting blood samples in blood tubes and interference tubes, which were subsequently centrifuged and the subsequent plasma split into two aliquots. Each blood tube had 250 μL of the platelet aliquot removed and assessed for platelet analysis. Additionally, each blood tube had blood films prepared, stained and reviewed. A second aliquot from the blood tubes were analyzed for coagulation parameters. The results of the analysis from three different donors are shown in Table 17.

TABLE 10

Hemolytic Potential

| Replicate | Donor 1 (Hematocrit (Hct) L/L) | Donor 2 (Hematocrit (Hct) L/L) | Donor 3 (Hematocrit (Hct) L/L) |
|---|---|---|---|
| 1 | 0.370 | 0.371 | 0.415 |
| 2 | 0.365 | 0.384 | 0.411 |
| 3 | 0.361 | 0.369 | 0.415 |
| Mean | 0.365 | 0.375 | 0.414 |
| SD | 0.00451 | 0.00814 | 0.00231 |
| CV (%) | 1.2 | 2.2 | 0.6 |

The blood samples showed platelet counts comparable to the negative control. This was confirmed by the visual examination of the blood film where no platelet clumps or other abnormalities were seen. No hemolysis was seen in tubes containing test item. The prothrombin time (PT), activated partial thromboplastin time (APTT) and Clauss fibrinogen (FibC) measured in tubes where blood had been mixed with test item showed no differences when compared to the results obtained from the negative controls. The results are shown in Table 18 and Table 19.

TABLE 11

Hemolysis

| Treatment | Sample ID | PLT Count ($x10^9$ cells/L) | Platelet Clump Flag (N = No clumps) | Blood Film (N = no clumps) | Hemoglobin | % Hemolysis |
|---|---|---|---|---|---|---|
| 0.4 mg/ml | 1-1 | 104 | N | N | 0 | 0 |
| Phenylephrine | 1-2 | 70 | N | N | 0 | 0 |
| Ratio 1:0.15 | 1-3 | 37 | N | N | 0 | 0 |
| 0.4 mg/ml | 2-1 | 87 | N | N | 0 | 0 |
| Phenylephrine | 2-2 | 65 | N | N | 0 | 0 |
| Ratio 1:0.3 | 2-3 | 38 | N | N | 0 | 0 |
| Negative | 3-1 | 93 | N | N | 0 | 0 |
| Control | 3-2 | 66 | N | N | 0 | 0 |
| Ratio 1:0.15 | 3-3 | 33 | N | N | 0 | 0 |
| Negative | 4-1 | 45 | N | N | 0 | 0 |
| Control | 4-2 | 57 | N | N | 0 | 0 |
| Ratio 1:0.3 | 4-3 | 27 | N | N | 0 | 0 |
| Positive | 5-1 | N/A | N/A | N/A | 6.0 | 100 |
| Control | 5-2 | N/A | N/A | N/A | 6.1 | 100 |
| Saponin | 5-3 | N/A | N/A | N/A | 6.7 | 100 |

TABLE 12

Fibrinogen, Prothrombin and APTT

| Treatment | Sample ID | Fibrinogen | Prothrombin | APTT |
|---|---|---|---|---|
| 0.4 mg/ml | 1-1 | 2.14 | 13.7 | 35.2 |
| Phenylephrine | 1-2 | 3.44 | 13.4 | 30.9 |
| Ratio 1:0.15 | 1-3 | 3.17 | 13.1 | 30.0 |
| 0.4 mg/ml | 2-1 | 3.42 | 15.3 | 37.8 |
| Phenylephrine | 2-2 | 2.64 | 15.0 | 32.3 |
| Ratio 1:0.3 | 2-3 | 2.42 | 14.7 | 32.3 |
| Negative | 3-1 | 2.06 | 13.9 | 34.8 |
| Control | 3-2 | 2.99 | 13.6 | 30.6 |
| Ratio 1:0.15 | 3-3 | 3.20 | 13.2 | 30.4 |
| Negative | 4-1 | 1.82 | 15.2 | 37.8 |
| Control | 4-2 | 2.74 | 14.7 | 32.2 |
| Ratio 1:0.3 | 4-3 | 2.99 | 14.7 | 32.3 |

Example 5: In Vivo Toxicity Study

A study was conducted to evaluate the toxicity of the ready-to-use, aseptically filled phenylephrine product of the present disclosure with the same proportion of components as listed in Table 1 above. The phenylephrine product was administered as a single dose intravenous infusion injected continuously for 24 hours to Wistar Han rats. The animals were either administered a control (0.9% sodium chloride for injection, USP [sterile saline]); 0.72 or 2.016 mg/kg/day of a commercially available reference phenylephrine hydrochloride product produced by Hikma Pharmaceuticals USA Inc. (0.02 mg/mL) ("reference"); or 0.72 or 8.64 mg/kg/day phenylephrine product of the disclosure (0.08, 0.2, or 0.4 mg/mL) ("test"). After dosing, animals were euthanized (interim sacrifice on Day 2) or observed for 14-days (terminal sacrifice on Day 15) to assess the reversibility or persistence of any effects.

Male and female Wistar Han rats were assigned to nine groups. Animals were dosed as a single dose on Day 1 via intravenous infusion into a femoral vein; dosing was controlled using a motorized syringe press or infusion pump set at a rate to provide the targeted daily dose, continuously for 24 hours.

Assessment of toxicity was based on mortality, clinical observations, body weights, food consumption, and clinical and anatomic pathology. Control animals remained below the limit of quantification at each time interval evaluated. Males generally had had higher exposure levels at all dose levels and concentrations when compared to females for both the test and reference. When comparing the 2 hour to 8 hour collections the plasma concentrations were generally consistent at each time interval collected with few exceptions. Mean plasma levels of phenylephrine are shown in Table 20.

TABLE 13

Toxicity

| Group/ Sex | Dose (mg/kg/day) | Concentration (mg/mL) | Rate (mL/kg/hr) | 2 hour (ng/ml) | 8 hour (ng/mL) |
|---|---|---|---|---|---|
| 1/M | 0 | 0 | 4.5 | <1 | <1 |
| 1/F | 0 | 0 | 4.5 | <1 | <1 |

TABLE 13-continued

Toxicity

| Group/Sex | Dose (mg/kg/day) | Concentration (mg/mL) | Rate (mL/kg/hr) | 2 hour (ng/ml) | 8 hour (ng/mL) |
|---|---|---|---|---|---|
| 2/Ma | 0.72 | 0.02 | 1.5 | 3.45 | 5.67 |
| 2/Fa | 0.72 | 0.02 | 1.5 | 2.21 | 2.18 |
| 3/M | 0.72 | 0.08 | 0.375 | 5.41 | 8.84 |
| 3/F | 0.72 | 0.08 | 0.375 | 1.85 | 2.44 |
| 4/M | 0.72 | 0.2 | 0.15 | 5.41 | 3.95 |
| 4/F | 0.72 | 0.2 | 0.15 | 1.85 | 4.48 |
| 5/M | 7.2 | 0.4 | 0.75 | 5.36 | 130.57 |
| 5/F | 7.2 | 0.4 | 0.75 | 26.58 | 24.78 |
| 6/Ma | 2.016 | 0.02 | 4.2 | 11.67 | 11.85 |
| 6/Fa | 2.016 | 0.02 | 4.2 | 5.89 | 6.50 |
| 7/M | 8.64 | 0.08 | 4.5 | 112.88 | 79.96 |
| 7/F | 8.64 | 0.08 | 4.5 | 22.74 | 27.76 |
| 8/M | 8.64 | 0.2 | 1.8 | 83.88 | 51.68 |
| 8/F | 8.64 | 0.2 | 1.8 | 22.13 | 27.46 |
| 9/M | 8.64 | 0.4 | 0.9 | 81.64 | 74.58 |
| 9/F | 8.64 | 0.4 | 0.9 | 24.93 | 478.6 |

Three females were sacrificed in a moribund condition on Day 1, 2, or 7 of the dosing phase, including one control female and one female each administered 0.72 or 2.016 mg/kg/day of the reference product. One male administered 0.72 mg/kg/day (0.4 mg/mL) was found dead on Day 1 of the dosing phase. One male administered 8.64 mg/kg/day (0.4 mg/mL) was found dead on Day 1. The cause of death for these animals could not be determined, but may be attributable to the blood collection procedure or surgical procedures. All other animals survived to their scheduled sacrifice.

No apparent phenylephrine product-related clinical observations, body weight changes, or food consumption changes were noted. No phenylephrine product-related effects on hematology, coagulation, or clinical chemistry test results were identified, compared with respective control and reference groups. No phenylephrine product-related mortality, organ weight differences, or macroscopic and microscopic observations were noted at either sacrifice, compared with control groups.

Due to the mild severity of findings and the lack of impact on the health and wellbeing of animals administered 8.64 mg/kg/day, effects for this dose were considered nonadverse. Thus, the no observed adverse effect level (NOAEL) is 8.64 mg/kg/day regardless of the rate of infusion or concentration of phenylephrine in the formulations.

It is to be understood that any particular aspect of the present disclosure that falls within the prior art may be excluded from any one or more of the claims. Since such aspects are deemed to be part of the whole of the present disclosure, any part of the whole disclosure may be excluded even if the exclusion is not set forth explicitly herein. Additionally, it is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A phenylephrine product comprising an aqueous phenylephrine solution comprising phenylephrine or a pharmaceutically acceptable salt thereof, a tonicity adjusting agent, and at least one buffering agent, wherein the phenylephrine solution does not contain sodium metabisulfite, wherein the phenylephrine solution has an osmolality of about 270-320 mOsmol/kg and is contained in an infusion bag comprising at least one port, wherein the phenylephrine or a pharmaceutically acceptable salt thereof is chemically stable for at least 24 months when the infusion bag is packaged in an overwrap with an oxygen absorber and stored at a controlled room temperature of 15-30° C. with relative humidity (RH) at about 40%±5%, and wherein the phenylephrine product is sterile and ready-to-use.

2. The phenylephrine product of claim 1, wherein the pharmaceutically acceptable salt is phenylephrine hydrochloride, and wherein the phenylephrine hydrochloride is at a concentration of about 0.05 to about 0.5 mg/ml.

3. The phenylephrine product of claim 2, wherein the phenylephrine hydrochloride is at a concentration selected from a group consisting of about 0.08 mg/ml, about 0.2 mg/ml, and about 0.4 mg/ml.

4. The phenylephrine product of claim 1, wherein the buffering agent comprises a citrate buffer.

5. The phenylephrine product of claim 1, wherein the pH of the phenylephrine solution is about 3.0 to about 6.5.

6. The phenylephrine product of claim 3, wherein the phenylephrine solution has an oxygen content of <1 ppm.

7. The phenylephrine product of claim 1, wherein the phenylephrine solution is free of one or more agents selected from the group consisting of a chelating agent, an antioxidant, a preservative, and a complexing agent.

8. The phenylephrine product of claim 1, wherein the infusion bag comprises a flexible multilayer film comprising a polymer selected from the group consisting of polyolefin, polyethylene, polypropylene, modified polyolefin-polyethylene polymers, styrene-polyolefin based polymers, block copolymers, or any combination thereof.

9. The phenylephrine product of claim 1, wherein the at least one port is closed with a twist-off closure comprising low density polyethylene (LDPE), polypropylene (PP), or a combination thereof.

10. The phenylephrine product of claim 1, wherein the at least one port is a tubing port, wherein the tubing port is used to fill the infusion bag with the phenylephrine solution.

11. The phenylephrine product of claim 10, wherein the tubing port is PVC and plasticizer free.

12. The phenylephrine product of claim 1, wherein the infusion bag comprises 2 to 7 layers of flexible polyolefin film.

13. The phenylephrine product of claim 1, wherein the average number of particles equal to or greater than 10 μm does not exceed 600 per 250 mL phenylephrine solution following storage at controlled room temperature for 24 months; and/or
the average number of particles equal to or greater than 25 μm does not exceed 60 per 250 mL phenylephrine solution following storage at controlled room temperature for 24 months.

14. The phenylephrine product of claim 1, wherein the oxygen content after storage at 40° C.±2° C. and 15% RH±5% for 6 months is less than 1 ppm; wherein the pH after storage at 40° C.±2° C. and 15% RH±5% for 6 months is about 3 to 6.5; and/or wherein the total impurities after storage at 40° C.±2° C. and 15% RH±5% for 6 months is less than 0.5%.

15. The phenylephrine product of claim 1, wherein the tonicity adjusting agent comprises sodium chloride, dextrose, glycerin, glycerol, mannitol, sorbitol, lactose, trehalose, potassium chloride, or a combination thereof.

16. The phenylephrine product of claim 1, wherein the tonicity adjusting agent comprises sodium chloride.

17. The phenylephrine product of claim 1, wherein the phenylephrine product is free of sulfite- or bisulfite-containing compounds and is antioxidant-free.

18. The phenylephrine product of claim 1, wherein the phenylephrine product does not affect prothrombin time (PT), activated partial thromboplastin time (APTT) and Clauss fibrinogen (FibC) of human blood cells compared to human blood cells not contacted by the phenylephrine product; and/or the phenylephrine product does not cause increased hemolysis of human platelets compared to human platelets not contacted by the phenylephrine product.

19. A method of preparing the phenylephrine product of claim 1, comprising:
   i) introducing a sterile infusion bag into an aseptic environment;
   ii) filling the sterile infusion bag with a sterile phenylephrine solution in the aseptic environment to produce an aseptically-filled infusion bag;
   iii) sealing the filled infusion bag in the aseptic environment; and
   iv) overwrapping the sealed infusion bag with an overwrap comprising an oxygen absorber and an oxygen indicator.

20. The method of claim 19, wherein the phenylephrine solution comprises about 0.05 to about 0.5 mg/ml phenylephrine or pharmaceutically acceptable salt thereof.

21. The method of claim 19, wherein the phenylephrine solution comprises phenylephrine hydrochloride at a concentration selected from a group consisting of about 0.08 mg/ml, about 0.2 mg/ml, and about 0.4 mg/ml.

22. A method of increasing blood pressure in a patient in need thereof, comprising administering the aqueous phenylephrine solution via the phenylephrine product of claim 1 to the subject; and wherein the aqueous phenylephrine solution is administered as a continuous infusion.

23. The method of claim 22, wherein the aqueous phenylephrine solution is phenylephrine hydrochloride administered at a rate of about 0.5 mcg/kg/min to about 6 mcg/kg/min.

24. A method of increasing blood pressure in a patient in need thereof, comprising administering the aqueous phenylephrine solution via the phenylephrine product of claim 1 to the subject; wherein the phenylephrine solution is administered as an intravenous bolus injection or infusion in a dosage of 50 mcg to 250 mcg of phenylephrine hydrochloride.

25. A method for increasing blood pressure in a patient in need thereof, comprising administering to the patient an aqueous phenylephrine solution via a phenylephrine product, wherein the phenylephrine product is stable, sterile and ready-to-use and comprises the phenylephrine solution contained in an infusion bag comprising at least one port; and wherein the phenylephrine solution comprises phenylephrine or a pharmaceutically acceptable salt thereof, a tonicity adjusting agent, and at least one buffering agent, wherein the phenylephrine solution does not contain sodium metabisulfite and does not contain a chelating agent, wherein the phenylephrine solution has an osmolality of about 270-320 mOsmol/kg, and wherein the phenylephrine solution does not cause increased hemolysis of human platelets compared to human platelets not contacted by the phenylephrine solution.

26. The method of claim 25, wherein the phenylephrine solution is administered to the patient at a rate of about 0.5 mcg/kg/min to about 6 mcg/kg/min.

27. The phenylephrine product of claim 2, wherein the phenylephrine solution is free of a chelating agent.

* * * * *